United States Patent
Vaezy et al.

(10) Patent No.: US 7,070,565 B2
(45) Date of Patent: Jul. 4, 2006

(54) SOLID HYDROGEL COUPLING FOR ULTRASOUND IMAGING AND THERAPY

(75) Inventors: Shahram Vaezy, Seattle, WA (US); Adrian Prokop, Lynnwood, WA (US); Roy W. Martin, Anacortes, WA (US); Peter Kaczkowski, Seattle, WA (US); Misty Noble, Seattle, WA (US)

(73) Assignee: University of Washington, Seattle, WA (US)

( * ) Notice: Subject to any disclaimer, the term of this patent is extended or adjusted under 35 U.S.C. 154(b) by 163 days.

(21) Appl. No.: 10/449,819

(22) Filed: May 30, 2003

(65) Prior Publication Data

US 2003/0233045 A1 Dec. 18, 2003

Related U.S. Application Data

(60) Provisional application No. 60/384,566, filed on May 30, 2002.

(51) Int. Cl.
*A61B 8/14* (2006.01)

(52) U.S. Cl. ...................................... 600/459

(58) Field of Classification Search ........ 600/407–472; 604/22, 267; 601/2, 3; 424/1.11, 9.5; 524/916
See application file for complete search history.

(56) References Cited

U.S. PATENT DOCUMENTS

| 5,039,774 A | | 8/1991 | Shikinami et al. ............. 528/60 |
| 5,065,742 A | | 11/1991 | Belikan et al. ................ 128/24 |
| 5,394,877 A | * | 3/1995 | Orr et al. ..................... 600/459 |
| 5,522,878 A | | 6/1996 | Montecalvo et al. ........ 607/152 |
| 5,833,647 A | * | 11/1998 | Edwards ........................ 604/22 |
| 6,039,694 A | | 3/2000 | Larson et al. ................ 600/459 |
| 6,491,672 B1 | * | 12/2002 | Slepian et al. .............. 604/267 |
| 6,685,639 B1 | * | 2/2004 | Wang et al. ................. 600/439 |
| 6,719,699 B1 | * | 4/2004 | Smith .......................... 600/459 |
| 6,846,291 B1 | * | 1/2005 | Smith et al. ................. 600/459 |
| 2004/0234453 A1 | * | 11/2004 | Smith .......................... 424/9.5 |

OTHER PUBLICATIONS

Vaezy, Shahram et al. 2001. "Acoustic surgery." *Physics World* (Aug.): 35-39.
Vaezy, Shahram et al. 2001. "Experimental Investigations and Device Development." First International Workshop on the Application of HIFU in Medicine. (May 10-13): 4pp.

* cited by examiner

*Primary Examiner*—Ali Imam
(74) *Attorney, Agent, or Firm*—Ronald M. Anderson

(57) ABSTRACT

The present invention employs hydrogels as acoustic couplings for clinical applications of ultrasound imaging and therapy, but is particularly applicable to high intensity focused ultrasound (HIFU) based therapy. While other materials can be used, it has been determined that polyacrylamide is sufficiently robust and transmissive to withstand the high temperatures encountered in HIFU therapy. One embodiment of a hydrogel coupling is configured in shape and size (length) to ensure that a focal region of an ultrasound transducer is disposed proximate the target area when the distal tip of the transducer is in contact with tissue. These couplings can be shaped to correspond to the beam focus characteristics of specific transducers. Water can be applied to hydrate the tip of the hydrogel coupling during use, and medication absorbed into the hydrogel material can be applied to the tissue in contact with the distal surface of the hydrogel.

45 Claims, 19 Drawing Sheets

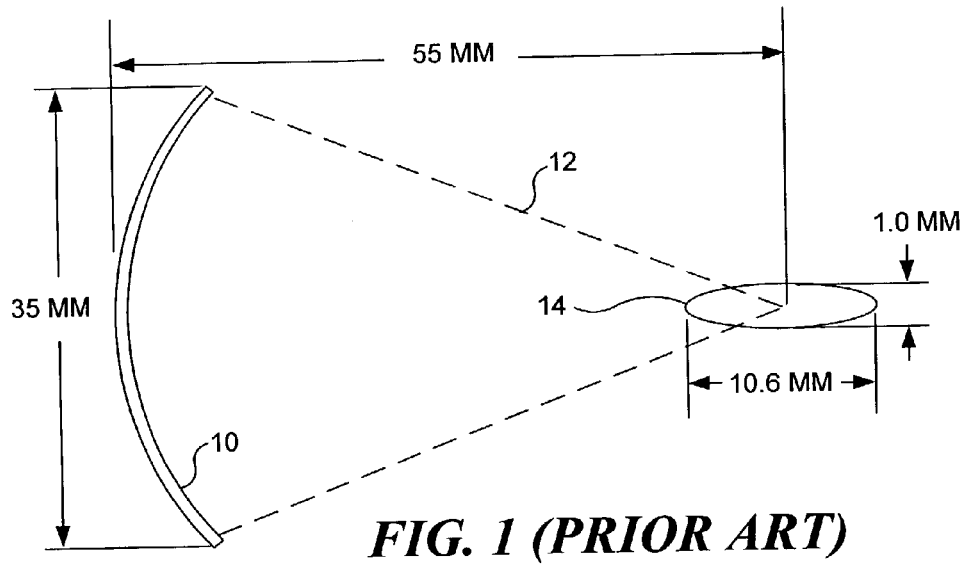
FIG. 1 (PRIOR ART)
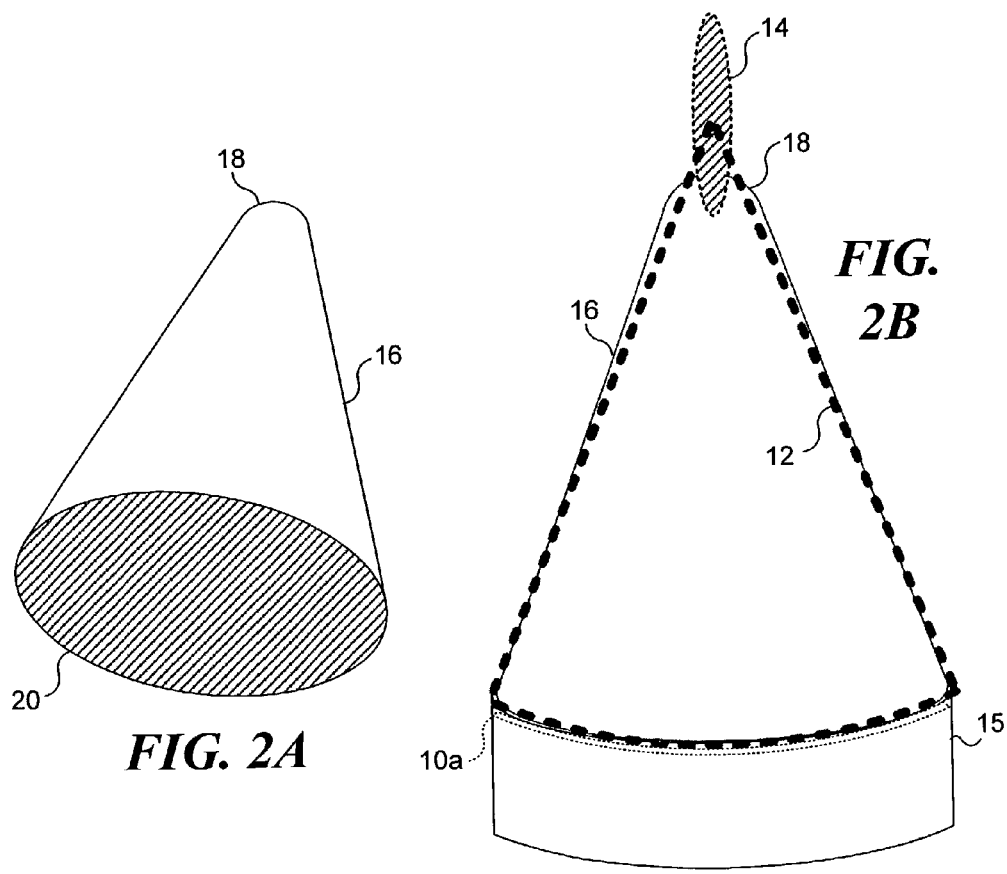
FIG. 2A
FIG. 2B

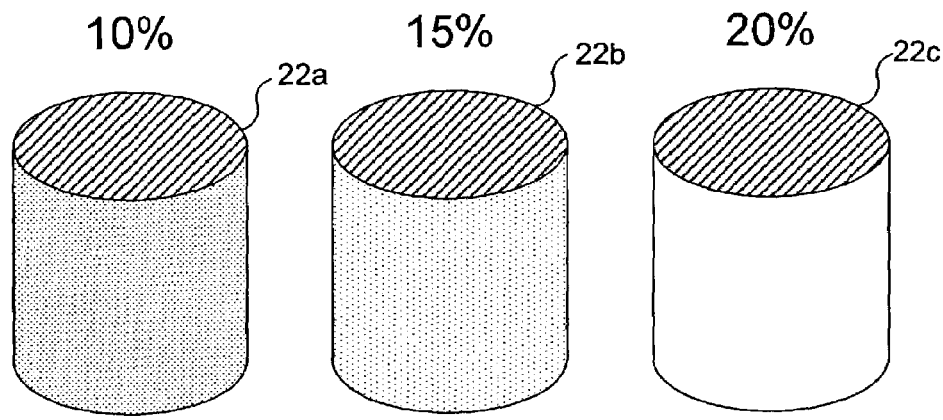
*FIG. 3A*  *FIG. 3B*  *FIG. 3C*
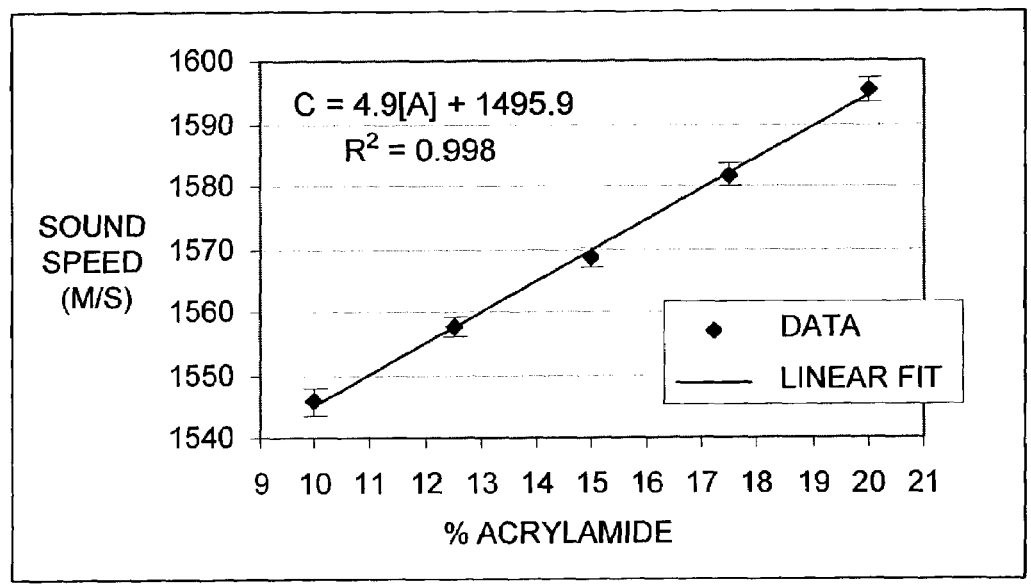
*FIG. 4A*

:::: LIQUID GEL
▓▓ SOLID GEL

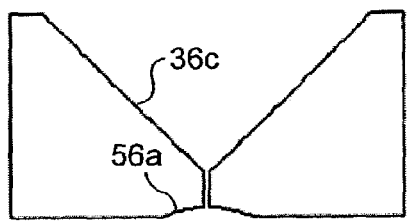
*FIG. 11B*
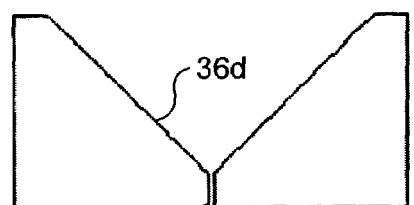
*FIG. 11C*
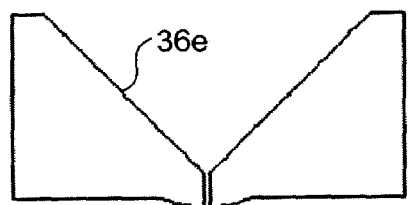
*FIG. 11D*

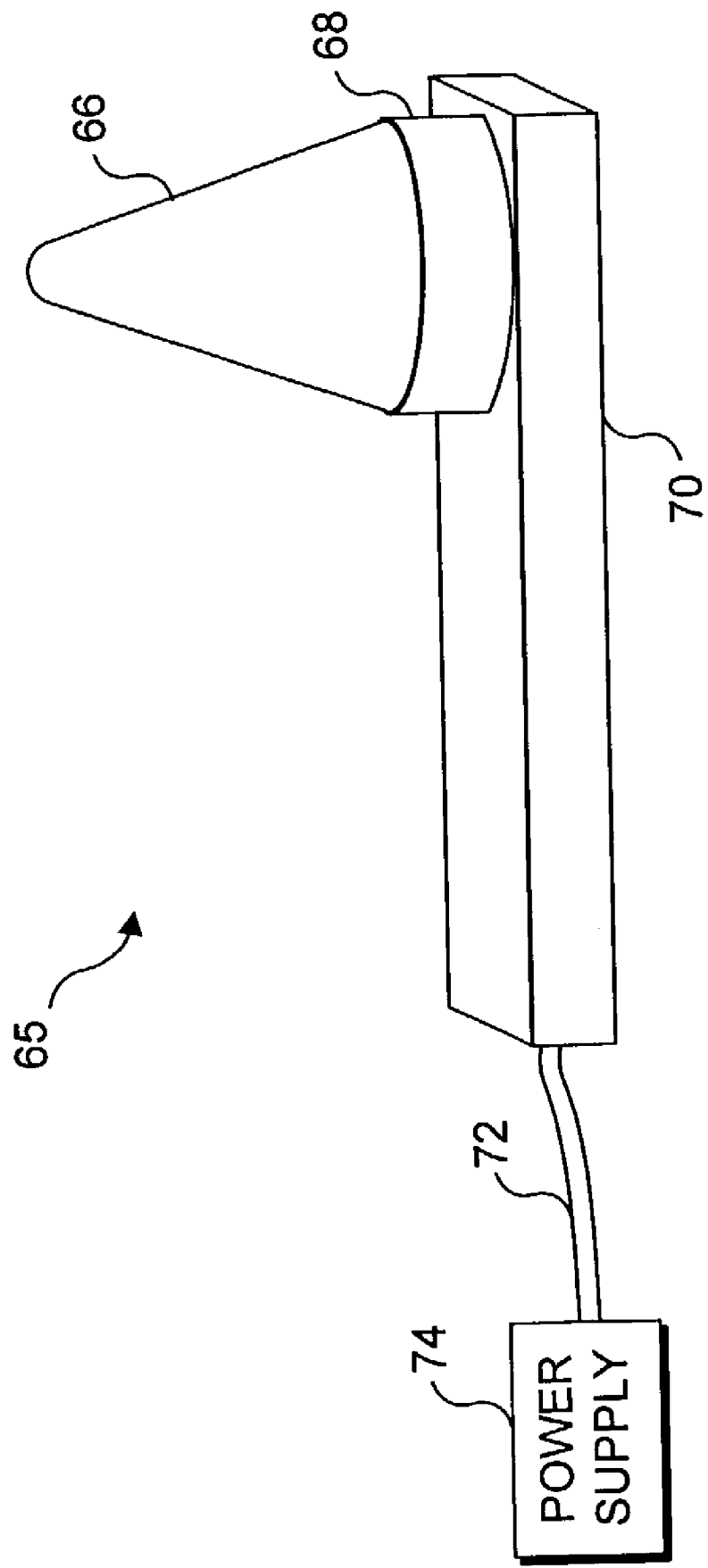

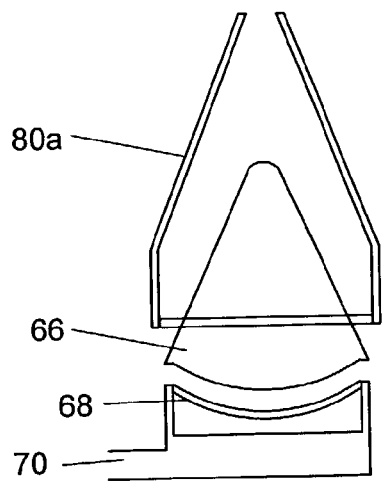
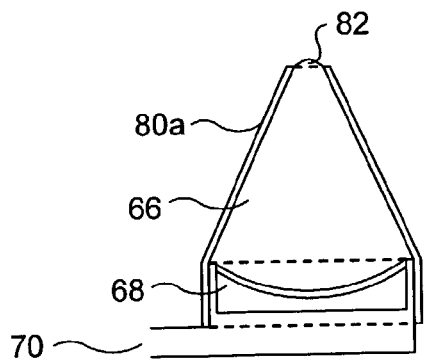
FIG. 13A  FIG. 13B
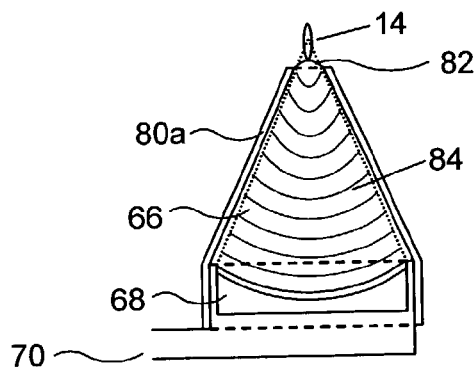
FIG. 13C
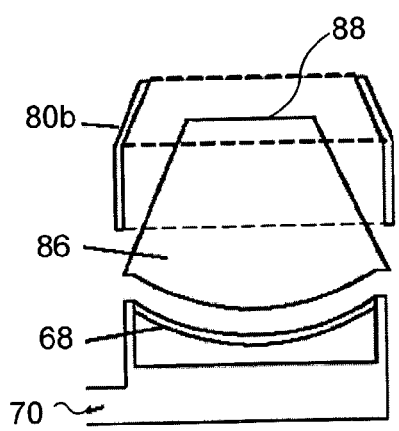
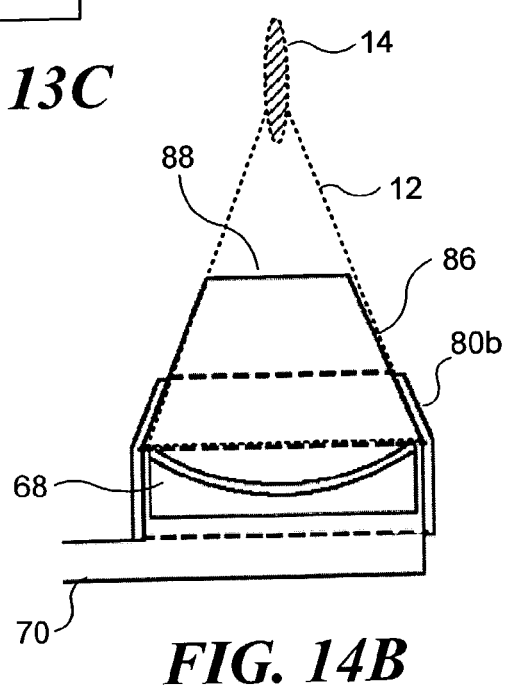
FIG. 14A  FIG. 14B

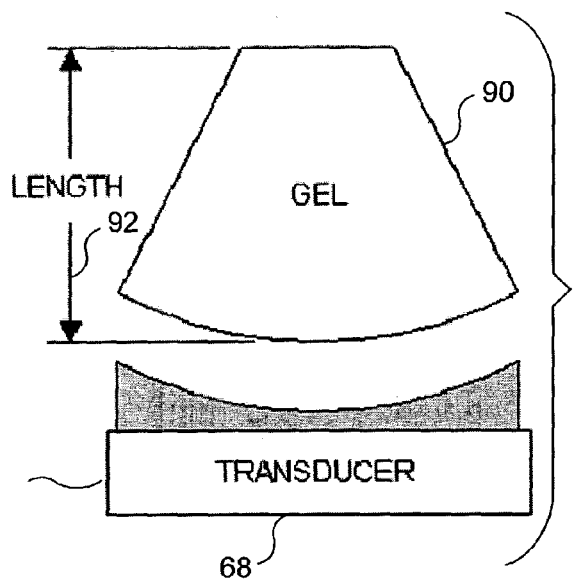
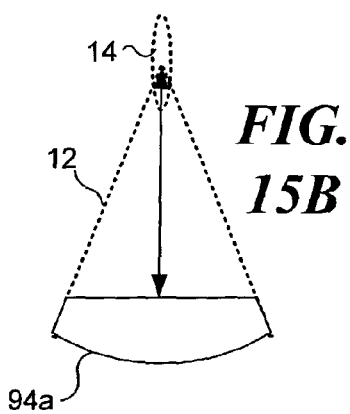
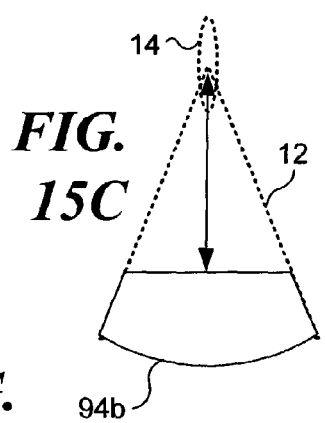
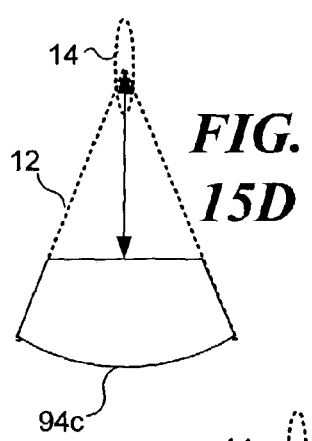
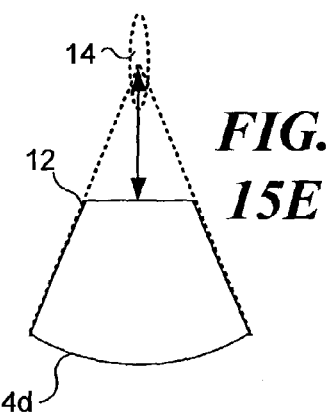
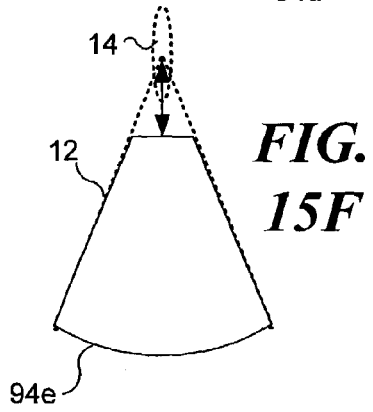
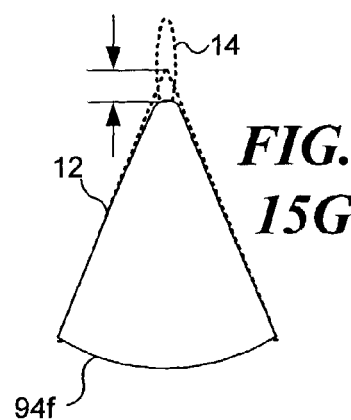

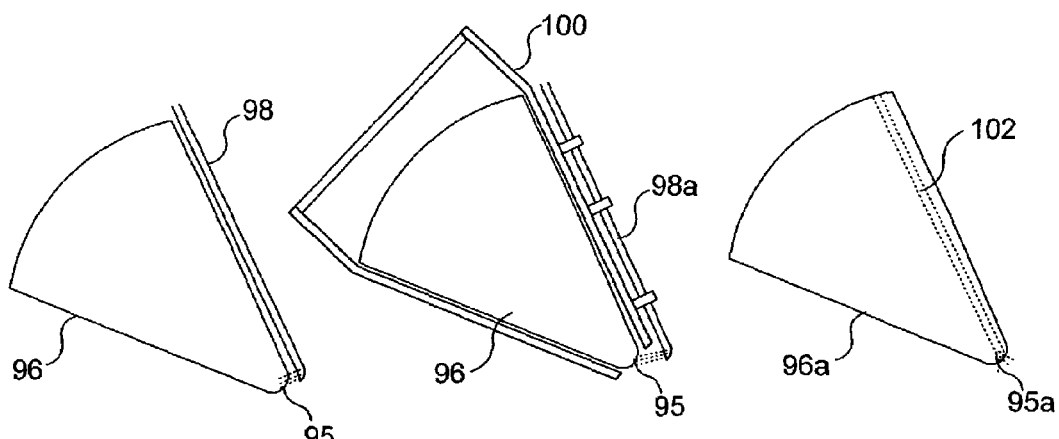
FIG. 17A  FIG. 17B  FIG. 17C
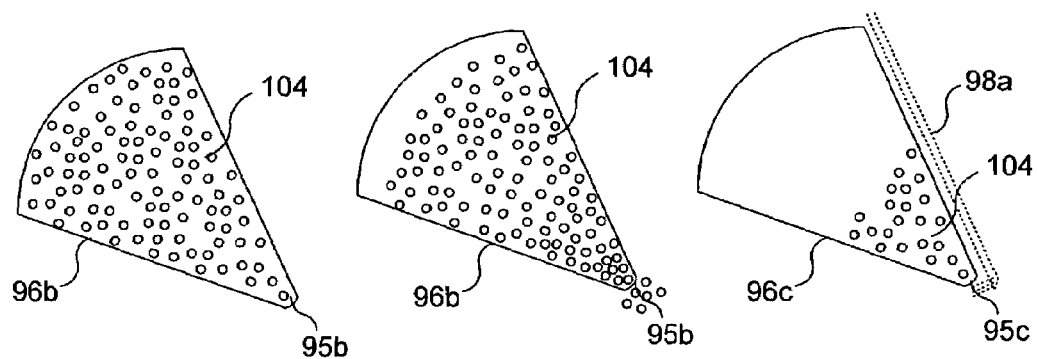
FIG. 18A  FIG. 18B  FIG. 18C
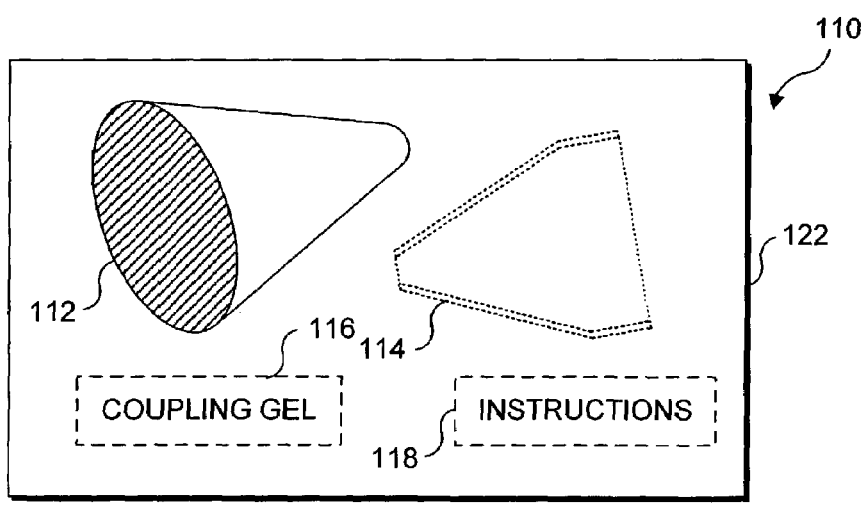
FIG. 19

SOLID HYDROGEL COUPLING FOR ULTRASOUND IMAGING AND THERAPY

RELATED APPLICATIONS

This application is based on a prior provisional application, Ser. No. 60/384,566, filed on May 30, 2002, the benefit of the filing date of which is hereby claimed under 35 U.S.C. § 119(e).

GOVERNMENT RIGHTS

The research for this invention was funded with a grant (N00014-96-1-0630) from the Department of the Navy, and with funding from the National Institutes of Health 5 R01 EB000292-04). The U.S. government may have certain rights in this invention.

FIELD OF THE INVENTION

The present invention generally relates to a hydrogel based coupling for use in ultrasonic imaging and therapy, and method for use of the same, and more specifically, pertains to a dimensionally stable hydrogel that remains stable when transmitting relatively high intensity ultrasound to a therapy site, and a method for using the same.

BACKGROUND OF THE INVENTION

Ultrasound is widely used for imaging a patient's internal structures without risk of exposure to potentially harmful radiation, as may occur when using X-rays for imaging. The first recorded use of ultrasound for imaging was by Dr. Karl Dussik, a Psychiatrist working at a hospital in Bad Ischl, Austria, who employed ultrasound to locate brain tumors. He used two opposed probes, including one for transmitting ultrasound waves, and the other for receiving them. With these probes, he transmitted an ultrasound beam through a patient's skull, and used the received signal to visualize the cerebral structure by measuring the ultrasound beam attenuation. He published a description of his technique in 1942, in an article entitled, "*Hyperphonography of the Brain.*"

Medical diagnostic equipment specially manufactured for using ultrasound became available in the 1950s. An ultrasound examination is a safe diagnostic procedure that uses high frequency sound waves to produce an image of the internal structures of a patient's body. Many studies have shown that these sound waves are harmless and may be used with complete safety, even to visualize the fetus in pregnant women, where the use of X-rays would be inappropriate. Furthermore, ultrasound examinations are sometimes quicker and typically less expensive than other imaging techniques.

More recently, the use of high intensity focused ultrasound (HIFU) for therapeutic purposes, as opposed to imaging, has received significant attention in the medical community. HIFU therapy employs ultrasound transducers that are capable of delivering 1,000–10,000 W/cm$^2$ to a focal spot, in contrast to diagnostic imaging ultrasound, where intensity levels are usually below 0.1 W/cm$^2$. A portion of the energy from these high intensity sound waves is transferred to the targeted location as thermal energy. The amount of thermal energy thus transferred can be sufficiently intense to cauterize undesired tissue, or to cause necrosis of undesired tissue (by inducing a temperature rise to beyond 70° C.) without actual physical charring of the tissue. Tissue necrosis can also be achieved by mechanical action alone (i.e., by cavitation that results in mechanical disruption of the tissue structure). Further, where the vascular system supplying blood to an internal structure is targeted, HIFU can be used to induce hemostasis. The focal region of this energy transfer can be tightly controlled so as to obtain necrosis of abnormal or undesired tissue in a small target area without damaging adjoining normal tissue. Thus, deep-seated tumors can be destroyed with HIFU without surgical exposure of the tumor site.

A particular advantage of HIFU therapy over certain traditional therapies is that HIFU is less invasive. The current direction of medical therapy is progressively toward utilizing less-invasive and non-operative approaches, as is evident from the increasing use of laparoscopic and endoscopic techniques. Advantages include reduced blood loss, reduced risk of infection, shorter hospital stays, and lower health care costs. HIFU has the potential to provide an additional treatment methodology consistent with this trend by offering a method of non-invasive surgery. Also, HIFU enables transcutaneous tumor treatment without making a single incision, thus avoiding blood loss and the risk of infection. Furthermore, HIFU therapy may be performed without the need for anesthesia, thereby reducing surgical complications and cost. Most importantly, these treatments may be performed on an outpatient basis, further reducing health care cost, while increasing patient comfort.

The use of HIFU for the destruction of tumors is a relatively new technique. The first clinical trials were performed on patients with hyperkinetic and hypertonic disorders (symptoms of Parkinson's disease). HIFU was used to produce coagulation necrosis lesions in specific complexes of the brain. While the treatment was quite successful, monitoring and guidance of the HIFU lesion formation was not easily achieved (as reported by N. T. Sanghvi and R. H. Hawes, (1994) "High-intensity focused ultrasound," *Gastrointestinal Endoscopy Clinics of North America*, 4:383–95).

Two HIFU-based systems have been developed for the treatment of benign prostatic hyperplasia (BPH) in humans (see the report by E. D. Mulligan, T. H. Lynch, D. Mulvin, D. Greene, J. M. Smith, and J. M. Fitzpatrick, (1997) "High-intensity focused ultrasound in the treatment of benign prostatic hyperplasia," *Br J Urol*, 70:177–80). These systems are currently in clinical use in Europe and Japan, and are undergoing clinical trials in the United States. Both systems use a transrectal HIFU probe to deliver 1,000–2,000 W/cm$^2$ to the prostate tissue through the rectum wall. No evidence of damage to the rectal wall has been observed during a rectoscopy, performed immediately after HIFU treatment (as reported by S. Madersbacher, C. Kratzik, M. Susani, and M. Marberger, (1994) "Tissue ablation in benign prostatic hyperplasia with high intensity focused ultrasound," *Journal of Urology*, 152:1956–60, discussion 1960–61). Follow-up studies have shown decreased symptoms of BPH (i.e., increased urinary flow rate, decreased post-void residual volume, and decreased symptoms of irritation and obstruction (see S. Madersbacher, C. Kratzik, N. Szabo, M. Susani, L. Vingers, and M. Marberger, (1993) "Tissue ablation in benign prostatic hyperplasia with high-intensity focused ultrasound," *European Urology*, 23: 1: 39–43).

HIFU has also been studied for the de-bulking of malignant tumors (C. R. Hill and G. R. ter Haar, (1995) "Review article: high intensity focused ultrasound-potential for cancer treatment," *Br J Radiol*, 68: 1296–1303), prostate cancer (S. Madersbacher, M. Pedevilla, L. Vingers, M. Susani, and M. Marberger, (1995) "Effect of high-intensity focused ultrasound on human prostate cancer in vivo," *Cancer Research*, 55: 3346–51), and testicular cancer (S. Madersbacher, C. Kratzik, M. Susani, M. Pedevilla, and M. Marberger, (1998) "Transcutaneous high-intensity focused ultrasound and irradiation: an organ-preserving treatment of cancer in a solitary testis," *European Urology*, 33:195–201) are among the cancers currently being investigated clinically for potential treatment with HIFU. An extensive clinical study to extracorporeally treat a variety of stage 4 cancers is underway in England (as noted by A. G. Visioli, I. H. Rivens, G. R. ter Haar, A. Horwich, R. A. Huddart, E. Moskovic, A. Padhani, and J. Glees, (1999) "Preliminary results of a phase I dose escalation clinical trial using focused ultrasound in the treatment of localized tumors," *Eur J Ultrasound*, 9: 11–18). The cancers involved include prostate, liver, kidney, hipbone, ovarian, breast adenoma, and ocular adenoma. No adverse effects, except one case of skin burn, have been observed.

An important component in any type of ultrasound therapy system is the mechanism for coupling the acoustic energy into the tissue. Good acoustic coupling is necessary to efficiently transfer the ultrasound energy from the transducer to the treatment site. The ideal acoustic coupler is a homogenous medium that has low attenuation and acoustic impedance similar to that of the tissue being treated. Due to its desirable acoustic transmission characteristics, water has commonly been used as the coupling medium in many therapeutic applications of ultrasound.

In previous hemostasis studies in which HIFU has been used to arrest bleeding of injured blood vessels and organs, the HIFU transducer was contained within a water-filled, conical, plastic housing with a thin, polyurethane membrane at the tip. This coupler was designed for superficial treatments, since it places the HIFU focus only several millimeters beyond the tip of the cone. While this coupling method has been useful for hemostasis experiments, it has many drawbacks that would make it impractical for a clinical setting. These disadvantages include degassing, sterilization, circulation, and containment issues. Due to the limitations of the current HIFU applicators, an alternative coupling medium is desirable.

Previous studies have shown hydrogels to be efficient coupling media for diagnostic ultrasound. Hydrogels are hydrophilic, cross-linked, polymer networks that become swollen by absorption of water. The high WC and favorable mechanical properties of hydrogels have made them attractive for a wide range of biomedical applications, including soft contact lenses, maxillofacial reconstruction, burn dressings, and artificial tendons. Since hydrogels consist mostly of water, they inherently have low attenuation and acoustic impedance similar to tissue. They can be formed into rigid shapes and have relatively low material costs.

Unlike the ultrasound transmission gels typically used for diagnostic scans, hydrogels can have consistencies similar to soft rubber, and can be formed into relatively rigid, three-dimensional (3-D) shapes. It would be desirable to provide hydrogel based couplings, methods for producing such hydrogel couplings, and methods for using such hydrogel couplings, wherein each coupling and each method is specifically configured for use in HIFU applications. It should be understood that because of the significant increase in power in HIFU as opposed to imaging, HIFU applications require much more robust couplers that can withstand the higher energy conveyed through the material, than is required in diagnostic or imaging applications.

Polyacrylamide (PA) gel has been employed as an acoustic coupler for non HIFU applications. The structure and properties of polyacrylamide have been extensively researched for the past 30 years. Currently, its most common biomedical application is gel electrophoresis for the separation of charged macromolecules. PA gel can have a very high WC, ranging from 70% to greater than 90% water by weight. The gel can be prepared relatively easily and quickly at room temperature. In addition, PA has been used for a variety of biomedical applications, and has been shown in many studies to have very good biocompatibility. An important consideration for any blood-contacting device is its resistance to causing thrombosis on its surface. Experiments have shown PA to exhibit no platelet adhesion. A recent clinical study that investigated the use of a PA-based blood filtration technique showed the material to have good blood compatibility, with no signs of hemolysis or blood clotting. It would thus be desirable to develop PA gel-based coupling materials, a method for making such materials, and a method for using such materials, where the materials are specifically configured for HIFU therapy applications.

SUMMARY OF THE INVENTION

A first aspect of the present invention is directed to a hydrogel coupling adapted to be disposed between an ultrasound transducer and a target, for use in acoustically coupling an ultrasound transducer with at least one of the target and a physical boundary associated with the target. Desirable targets might include surface tissue on a patient, as well as sub-dermal areas within a patient's body. Thus, the physical boundary can be the dermal layer of a patient, and the target area can be a sub-dermal area, so that the acoustic transducer must be coupled with the dermal layer. The acoustical energy generated by the transducer must then move through the coupling, through the dermal layer (the physical boundary), and be focused on the target.

Furthermore, the target or physical boundary may also represent the wall of an internal body cavity. For example, a probe including an ultrasound transducer and a hydrogel coupling in accord with the present invention may be inserted into a body cavity, so that the hydrogel coupling acoustically couples the acoustic transducer to the wall of the body cavity. Depending on the focal length of the ultrasound transducer, the focal region can be proximate the wall, in which case the wall is the target. In other cases, the focal region can be beyond the wall, in which case the wall is the physical boundary, and the target is beyond the wall.

In some cases, a probe may be surgically inserted into a patient, such that the hydrogel coupling of the present invention couples to internal tissues. As with the cavity wall noted above, such internal tissue can be considered either a boundary or a target, depending on the focal length of the acoustic transducer and the size and shape of the hydrogel coupling, and the location of the tissue to be treated.

In a first aspect of the present invention, the hydrogel coupling includes a dimensionally stable hydrogel mass having a proximal surface configured to be disposed adjacent to an ultrasound transducer, and a distal surface configured to acoustically couple with at least one of a target and a physical boundary associated with a target. A distance between the proximal surface and an outer extent of the distal surface of the dimensionally stable hydrogel mass (i.e., its length) is selected to ensure that a focal region of an ultrasound transducer is disposed proximate a target. In some cases, the target will be proximate a boundary such as a dermal layer or a cavity wall, and the distance will differ from the focal length of the acoustic transducer by a relatively small amount. In other cases, the target will be disposed beyond such a boundary, and the distance will be selected to ensure that when the dimensionally stable hydrogel mass is disposed between the acoustic transducer and the boundary, such that when the acoustic transducer is coupled with the boundary, the focal region of the acoustic transducer is proximate the target. Longer focal lengths will require a dimensionally stable hydrogel mass having a greater length. By selecting a dimensionally stable hydrogel mass having an appropriate length, the focal region will overlap the target.

Preferably, the proximal surface of the dimensionally stable hydrogel mass is further configured to conform to an outer surface of an ultrasound transducer. In some embodiments, the proximal surface is convex in shape. The distal surface of the dimensionally stable hydrogel mass can be shaped as desired. Beneficial distal surface shapes include concave surfaces, convex surfaces and flat surfaces. The body of the dimensionally stable hydrogel mass (i.e., the portion between the proximal and distal surfaces) can be shaped as desired. A generally cone shaped, dimensionally stable hydrogel mass is likely to be preferred, since the acoustic beam from an ultrasonic transducer configured for applying HIFU is generally focused to a cone shape, starting out with a broad footprint near the ultrasonic transducer, and narrowing to a small focal region. Dimensionally stable hydrogel masses in the shapes of cones and truncated cones have been empirically determined to be useful.

In at least one embodiment, the dimensionally stable hydrogel mass is substantially transparent, to avoid blocking a view of a target when in use. This characteristic facilitates the use of the hydrogel coupling, since a clinician will be able to see through the dimensionally stable hydrogel mass, to verify where the outer extent of the distal surface is contacting the boundary or the target.

Some embodiments of hydrogel couplings in accord with the present invention include a retaining housing configured to removably couple the dimensionally stable hydrogel mass to an ultrasound transducer. Thus, dimensionally stable hydrogel masses can be used, removed, discarded, and replaced with another dimensionally stable hydrogel mass. Preferably, the retaining housing substantially conforms to an outer surface of the dimensionally stable hydrogel mass. The retaining housing can substantially enclose the dimensionally stable hydrogel mass, except for the outer extent of the distal surface and the proximal surface. Tie retaining housing is preferably formed from a polymer material.

The dimensionally stable hydrogel mass can be made from poly(2-hydroxyethyl methacrylate), PA, or combinations thereof. When PA is used to produce dimensionally stable hydrogel masses, an amount of acrylamide monomer employed in the mass can be varied such that an acoustical impedance of the dimensionally stable hydrogel mass substantially corresponds to an acoustical impedance of at least one of the target and the physical boundary associated with the target with which the dimensionally stable hydrogel mass is to acoustically couple.

One particularly beneficial embodiment of a hydrogel coupling in accord with the present invention includes a dimensionally stable hydrogel mass having a melting point that is sufficiently high, and an acoustical absorbance that is sufficiently low to enable the dimensionally stable hydrogel mass to maintain its structural integrity when employed to couple an acoustic transducer with at least one of a target and a physical boundary associated with a target, under the following conditions: (a) the transducer is energized for a period ranging from about 1 second to about 100 seconds; and, (b) the intensity of the acoustical beam generated by the transducer ranges from about 100 W/cm2 to about 10,000 W/cm2.

Other embodiments of the present invention will include means to hydrate the dimensionally stable hydrogel mass. The mass can be hydrated with a fluid channel having a proximal end configured to be coupled to a water supply, and having a distal end disposed adjacent to the outer extent of the distal surface. Such a fluid channel is preferably included within the dimensionally stable hydrogel mass. For embodiments that include a retaining housing, at least a portion of the fluid channel can be coupled with, or integral to, the retaining housing.

Yet another embodiment of the first aspect of the present invention includes means to deliver a medicinal agent outside the distal surface of the dimensionally stable hydrogel mass, which includes a fluid channel having a distal end configured to be coupled to a fluid supply of a medicinal agent, the fluid channel having a distal end extending through the distal surface, alternatively, a quantity of a medicinal agent disposed within the dimensionally stable hydrogel mass.

When the dimensionally stable hydrogel mass includes the medicinal agent, the medicinal agent can be distributed substantially evenly throughout the dimensionally stable hydrogel mass, or can be distributed proximate the distal surface of the dimensionally stable hydrogel mass.

A related aspect of the present invention is directed to a hydrogel coupling that is adapted to be disposed between an ultrasound transducer and at least one of a target and a physical boundary associated with a target, to acoustically couple the ultrasound transducer with at least one of the target and the physical boundary associated with the target. In this second aspect of the present invention, the dimensionally stable hydrogel mass has a melting point that is sufficiently high, and an acoustical absorbance that is sufficiently low to enable the dimensionally stable hydrogel mass to maintain its structural integrity when employed to couple an acoustic transducer to at least one of the target and the physical boundary associated with a target, under the following conditions: (a) the transducer is energized for a period ranging from about 1 second to about 100 seconds, and (b) the intensity of the acoustical beam at the focal region of the transducer ranges from about 100 W/cm$^2$ to about 10,000 W/cm$^2$.

In common with each embodiment of the first aspect of the invention, in each embodiment of the second aspect of the invention the dimensionally stable hydrogel mass has a proximal surface configured to be disposed adjacent to an ultrasound transducer, and a distal surface configured to acoustically couple with at least one of the target and the physical boundary associated with the target. However, in each embodiment of this second aspect of the invention, the separation between the first and second portion is not required to be controlled, although if desired, it can be.

As with the first aspect of the invention, the distal and proximal surfaces of the dimensionally stable hydrogel mass can be configured as desired, so that the proximal surface is configured to conform to an outer surface of an ultrasound transducer, and the distal surface may be convex, concave, or flat.

Yet another aspect of the present invention is directed to a kit containing components to be used to acoustically couple an ultrasound transducer with a target, wherein the ultrasound transducer is configured to apply HIFU to a target. The kit includes at least a dimensionally stable hydrogel mass having a proximal surface configured to be disposed adjacent to an ultrasound transducer that is designed to produce HIFU applied to a target, and a distal surface having an outer extent configured to acoustically couple with at least one of a target and a boundary associated with the target, where the boundary is disposed between the ultrasound transducer and the target. The kit also includes at least a sealed package configured to maintain the dimensionally stable hydrogel mass in a hydrated condition until the dimensionally stable hydrogel mass is removed from the sealed package in preparation for use.

In at least one embodiment, the sealed package is further configured to maintain the dimensionally stable hydrogel mass in a sterile condition until the dimensionally stable hydrogel mass is removed from the sealed package in preparation for use. The sealed package is preferably hermetically sealed and/or vacuum-sealed.

Some embodiments of such a kit will include instructions for using the dimensionally stable hydrogel mass to couple an ultrasound transducer with a target, to facilitate an application of HIFU to a target. The instructions will at least inform users how to maintain the distal surface of the dimensionally stable hydrogel mass in a hydrated condition. At least one embodiment of the kit will include a semisolid or fluidic coupling medium to be used to enhance an acoustic coupling of the lower surface of the dimensionally stable hydrogel mass to an outer surface of an ultrasound transducer that will apply HIFU.

The kit can include any combination of: (1) a retaining housing configured to removably couple the dimensionally stable hydrogel mass with an ultrasound transducer; (2) means to hydrate the distal surface of the dimensionally stable hydrogel mass; (3) means to deliver a medicinal fluid proximate the distal surface of the dimensionally stable hydrogel mass; and, (4) a fluid channel having a proximal end configured to couple to a fluid supply, and a distal end configured to be disposed proximate the distal end of the dimensionally stable hydrogel mass.

Still another aspect of the present invention is directed to a method for using a dimensionally stable hydrogel mass to acoustically couple an ultrasound transducer with at least one of a target and a physical boundary associated with the target, wherein the ultrasound transducer is configured to apply HIFU to a target. The method includes the steps of selecting an input power level and a duration to be used to energize the ultrasound transducer, and providing a dimensionally stable hydrogel mass capable of maintaining its structural integrity when used to couple the ultrasound transducer with at least one of the target and a physical boundary associated with the target, using the input power level and for the duration selected. Further steps of the method include coupling a proximal surface of the dimensionally stable hydrogel mass to an outer surface of the ultrasound transducer and coupling an outer extent of the distal surface of the dimensionally stable hydrogel mass to at least one of the target and the physical boundary separating the target from the distal surface of the dimensionally stable hydrogel mass.

Once the coupling is complete, the step of energizing the ultrasound transducer at the selected input power level and for the selected duration is performed, the dimensionally stable hydrogel mass acoustically coupling the acoustic transducer to at least one of a target and a physical boundary separating the target from the distal surface of the dimensionally stable hydrogel mass.

Additional steps can include hydrating the distal surface of the dimensionally stable hydrogel mass, to prevent damage to the distal surface of the dimensionally stable hydrogel mass by the HIFU, and/or delivering a medicinal agent to at least one of the target and the physical boundary, after coupling the distal surface of the dimensionally stable hydrogel mass to at least one of the target and the physical boundary.

In at least one embodiment, the step of providing a dimensionally stable hydrogel mass includes the step of selecting a dimensionally stable hydrogel mass in which a length between the lower surface and the distal surface of the dimensionally stable hydrogel mass will ensure that a focal region of the ultrasound transducer is disposed proximate the target.

In other embodiments, the step of providing a dimensionally stable hydrogel mass includes the step of selecting a dimensionally stable hydrogel mass that has a melting point sufficiently high, and an acoustical absorbance sufficiently low to enable the dimensionally stable hydrogel mass to maintain its structural integrity when employed to couple an acoustic transducer to a target, under the following conditions: (a) the transducer is energized for a period ranging from about 1 second to about 100 seconds, and (b) the intensity of the acoustical beam at the focal region of the transducer ranges from about 100 W/cm2 to about 10,000 W/cm2.

The step of coupling a proximal surface of the dimensionally stable hydrogel mass to an outer surface of the ultrasound transducer can include the step of using a retaining housing to removably couple the dimensionally stable hydrogel mass with the ultrasound transducer. The retaining housing substantially encompasses each surface of the dimensionally stable hydrogel mass, except for the proximal surface and the outer extent of the distal surface.

Still another aspect of the present invention is directed to a method for making a dimensionally stable hydrogel mass to acoustically couple with an ultrasound transducer configured to apply HIFU to a target, wherein the dimensionally stable hydrogel mass includes a proximal surface configured to couple with an ultrasound transducer and a distal surface configured to couple with at least one of a target and a physical boundary separating the target from the ultrasound transducer. The method includes the steps of providing at least one monomer capable of forming a dimensionally stable hydrogel mass when polymerized and hydrated, providing an agent for inducing polymerization of the at least one monomer, providing a quantity of water sufficient to hydrate the quantity of the at least one monomer that will be polymerized, and providing a mold configured to form a dimensionally stable hydrogel mass to a desired size and shape.

The dimensionally stable hydrogel mass is produced by mixing appropriate quantities of each monomer, the agent for inducing polymerization, and water together to form a mixture, introducing the mixture into the mold, and allowing the mixture to polymerize in the mold. Once polymerization is complete, the dimensionally stable hydrogel mass is removed from the mold.

In at least one embodiment, the mold includes reservoir and a mold volume which are in fluid communication. The mold volume conforms to the desired size and shape of the dimensionally stable hydrogel mass to be produced. In such an embodiment, the mixture is introduced into the mold via the reservoir, until the mold volume is filled with the mixture, and additional mixture is in the reservoir. Polymerization of the mixture in the reservoir is inhibited, while polymerization of the mixture in the mold volume is allowed. The polymerization reduces the volume of the mixture in the mold volume, so that more of the mixture in the reservoir flows into the mold volume and polymerizes. Once the mold volume is filled with a polymerized dimensionally stable hydrogel mass, the mixture in the reservoir volume is allowed to polymerize. The dimensionally stable hydrogel mass is removed from the mold, and any undesired portion of the dimensionally stable hydrogel mass (i.e. the portion corresponding to the reservoir) is removed.

In at least one embodiment, the step of inhibiting the polymerization of the mixture in the reservoir includes the step of stirring the mixture in the reservoir. Preferably, the reservoir is disposed above a portion of the mold volume corresponding to the distal surface of the desired dimensionally stable hydrogel mass. The reservoir can be shaped to produce a dimensionally stable hydrogel mass whose distal surface is convex, flat, or concave.

The method preferably uses at least one monomer and an agent for inducing polymerization, which have been selected to produce a dimensionally stable hydrogel mass that has a desired melting point and a desired acoustical absorbance, so as to enable the dimensionally stable hydrogel mass to maintain its structural integrity when employed to couple an acoustic transducer to a target under predefined conditions.

A fluid channel is preferably formed within the dimensionally stable hydrogel being produced.

Optionally, the method can include the step of adding a medicinal agent to the mixture before the mixture is introduced into the mold, such that the dimensionally stable hydrogel mass produced includes a medicinal agent. The medicinal agent can be added to the dimensionally stable hydrogel mass after it has polymerized.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1 (Prior Art) schematically illustrates dimensions and beam characteristics of a 3.5 MHz acoustic transducer that is capable of being used for HIFU therapeutic applications;

FIG. 2A schematically illustrates an exemplary shape for hydrogel couplings in accord with the present invention;

FIG. 2B schematically illustrates how closely the exemplary shape of the hydrogel coupling shown in FIG. 2A corresponds to the focused beam characteristics of the acoustic transducer of FIG. 1;

FIG. 3A schematically illustrates a polyacrylamide (PA) gel coupler in accord with the present invention, produced using 10% acrylamide monomer;

FIG. 3B schematically illustrates a PA gel coupler in accord with the present invention, produced using 15% acrylamide monomer;

FIG. 3C schematically illustrates a PA gel coupler in accord with the present invention, produced using 20% acrylamide monomer;

FIG. 4A is a graphical representation of sound speed in PA hydrogel couplings versus acrylamide concentration, showing a linear data fit;

Figure 7:
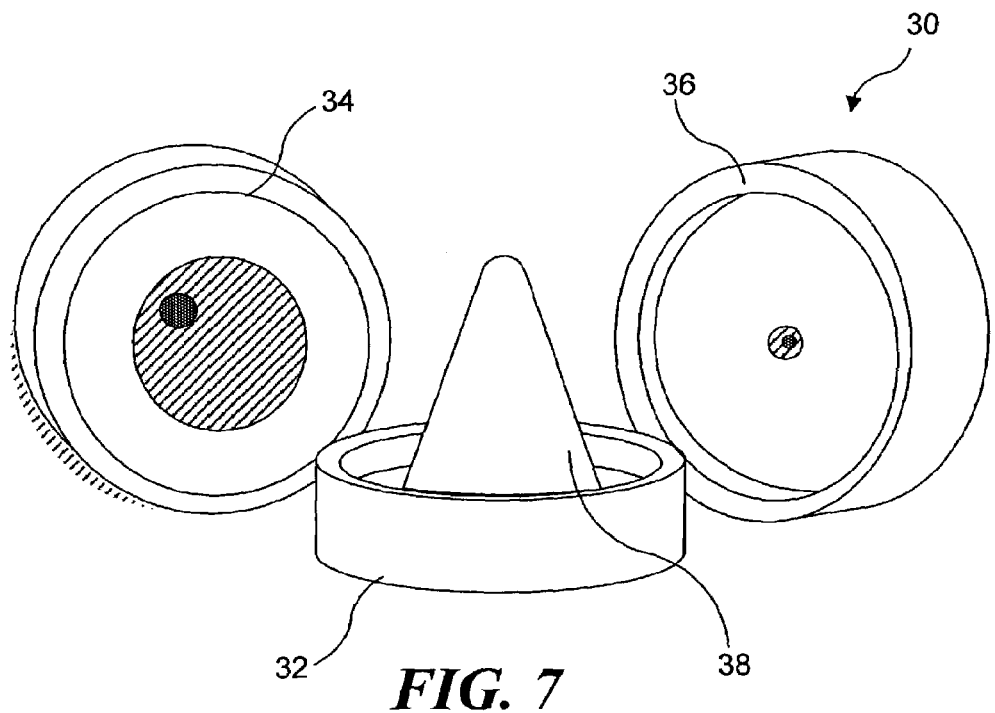
Figure 8:
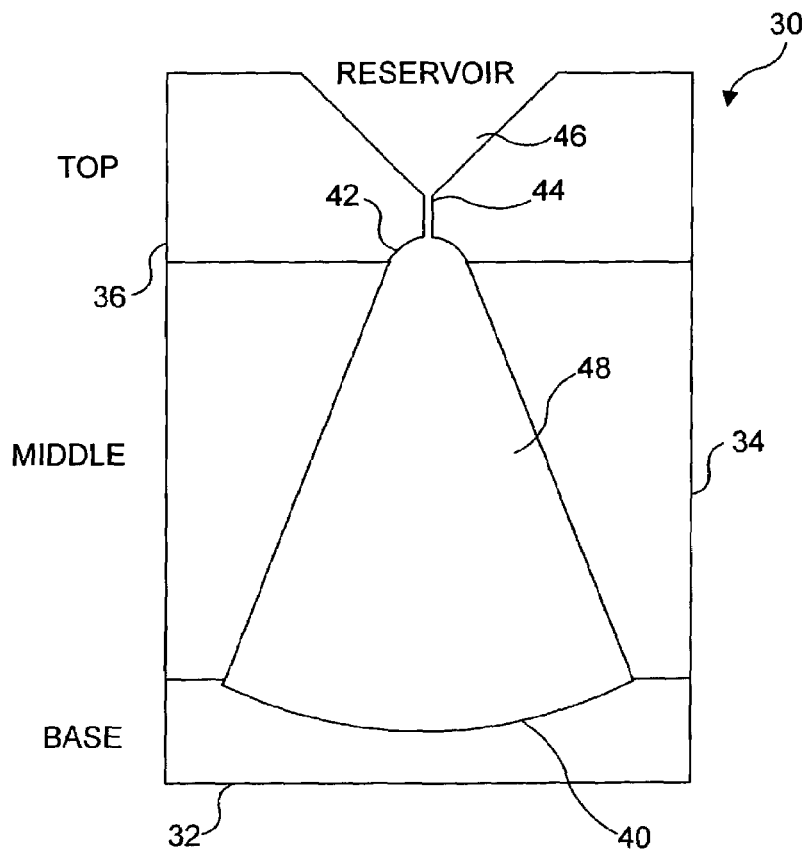
Figure 9A:
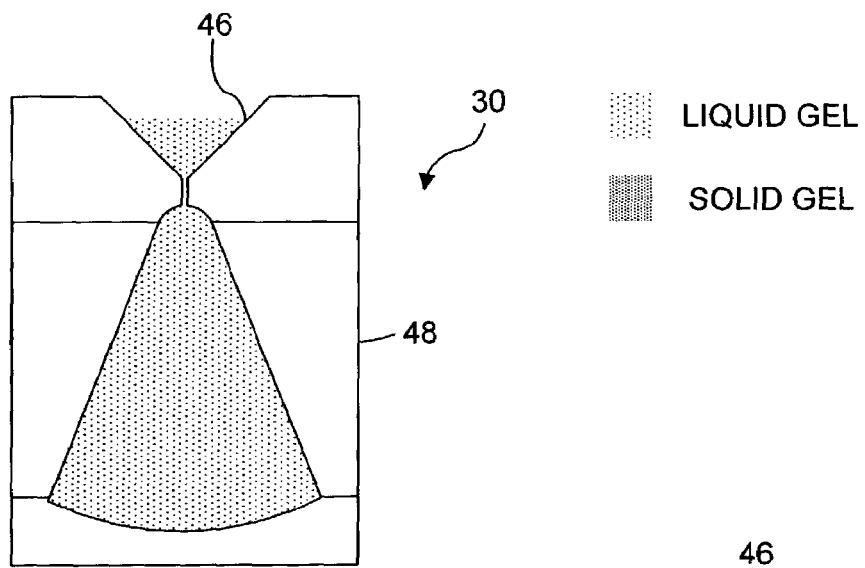
Figure 9B:
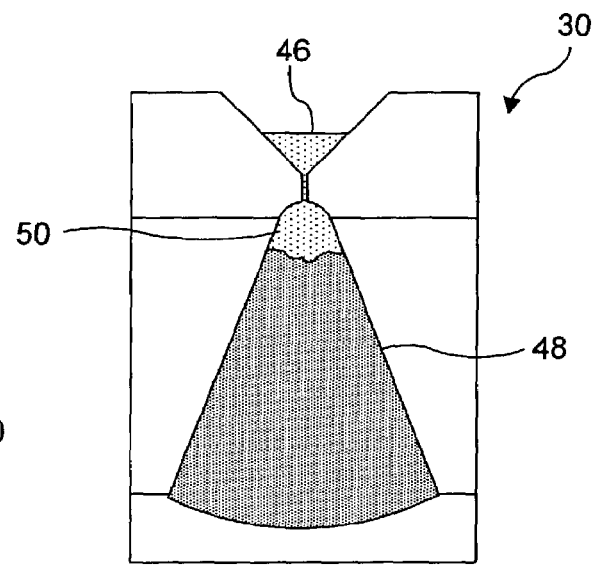
Figure 9C:
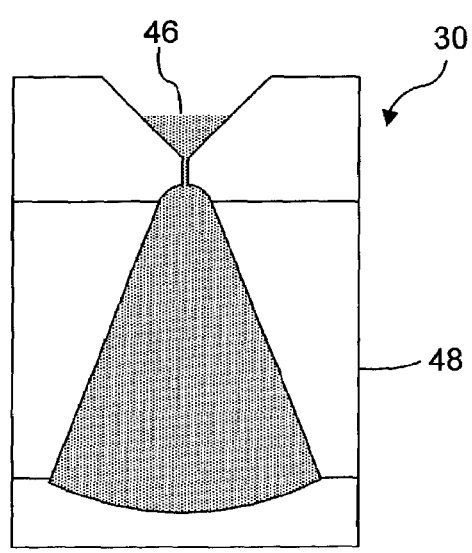
Figure 10A:
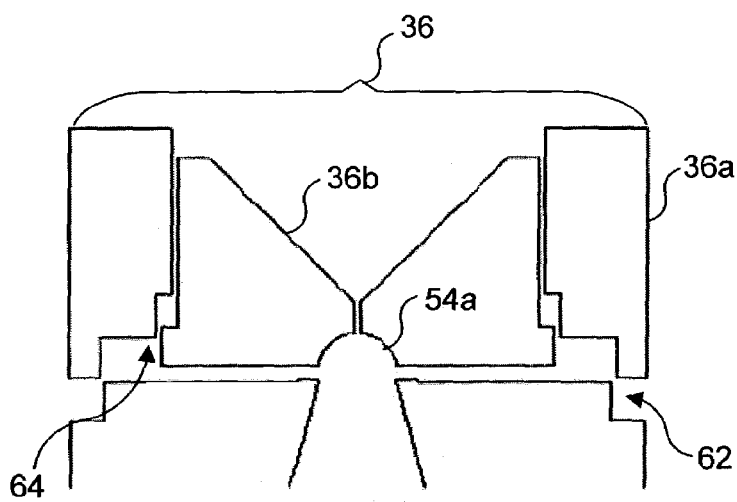
Figure 10B:
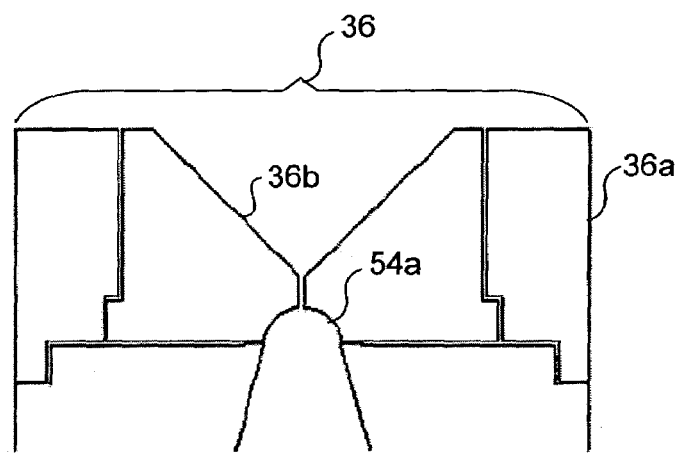
Figure 12B:
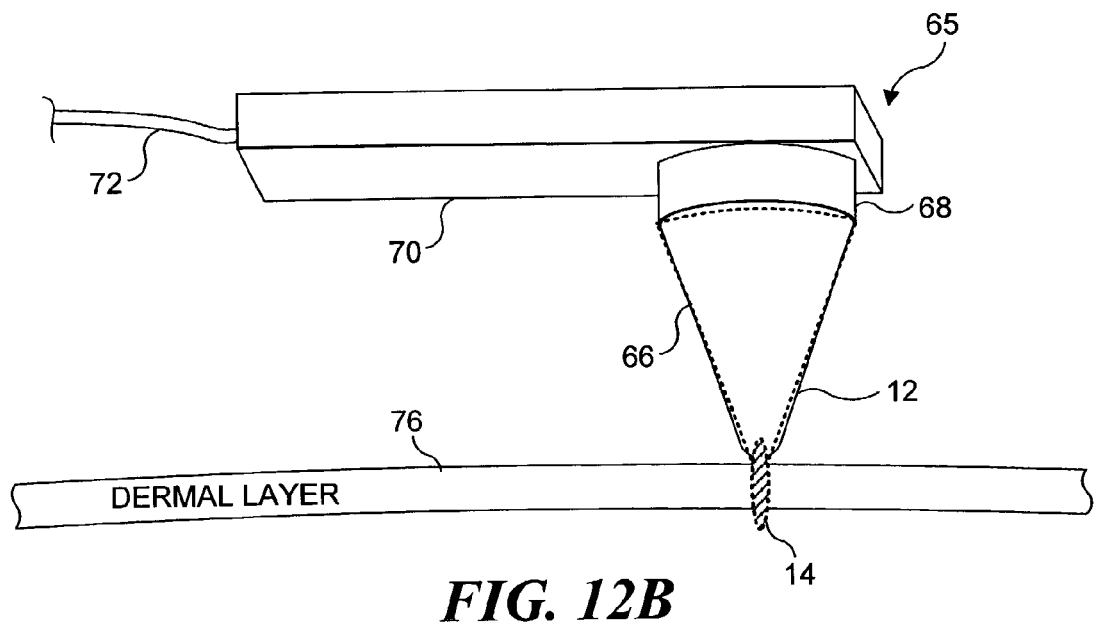
Figure 12C:
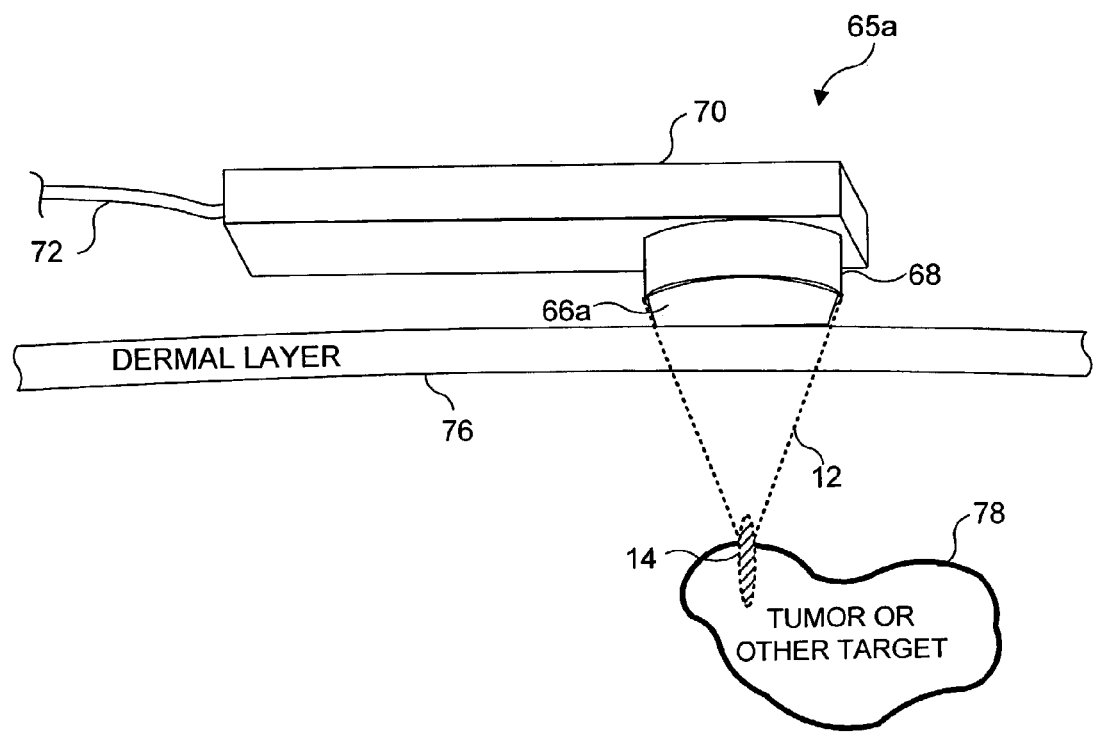
Figure 16:
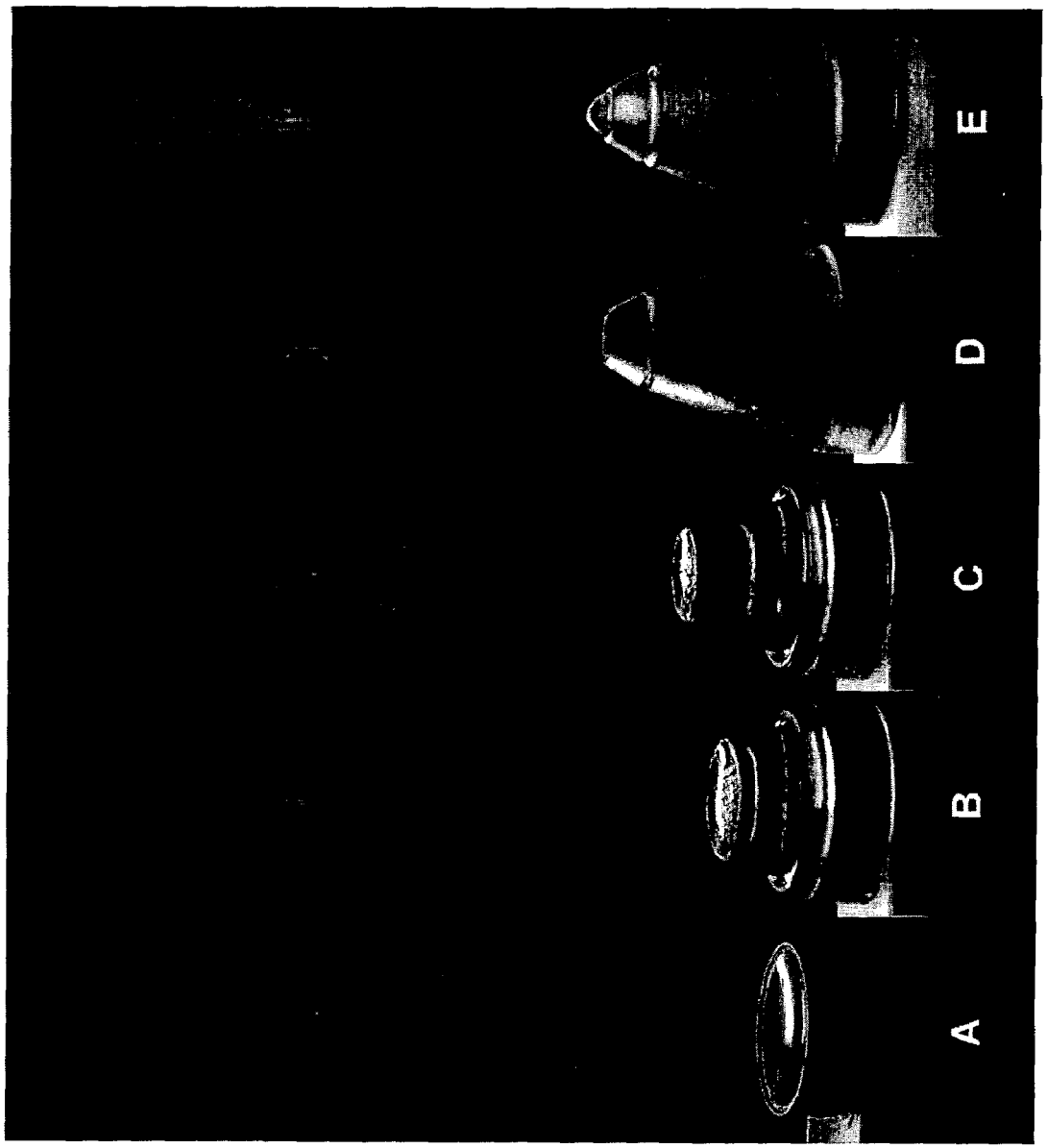
Figure 20:
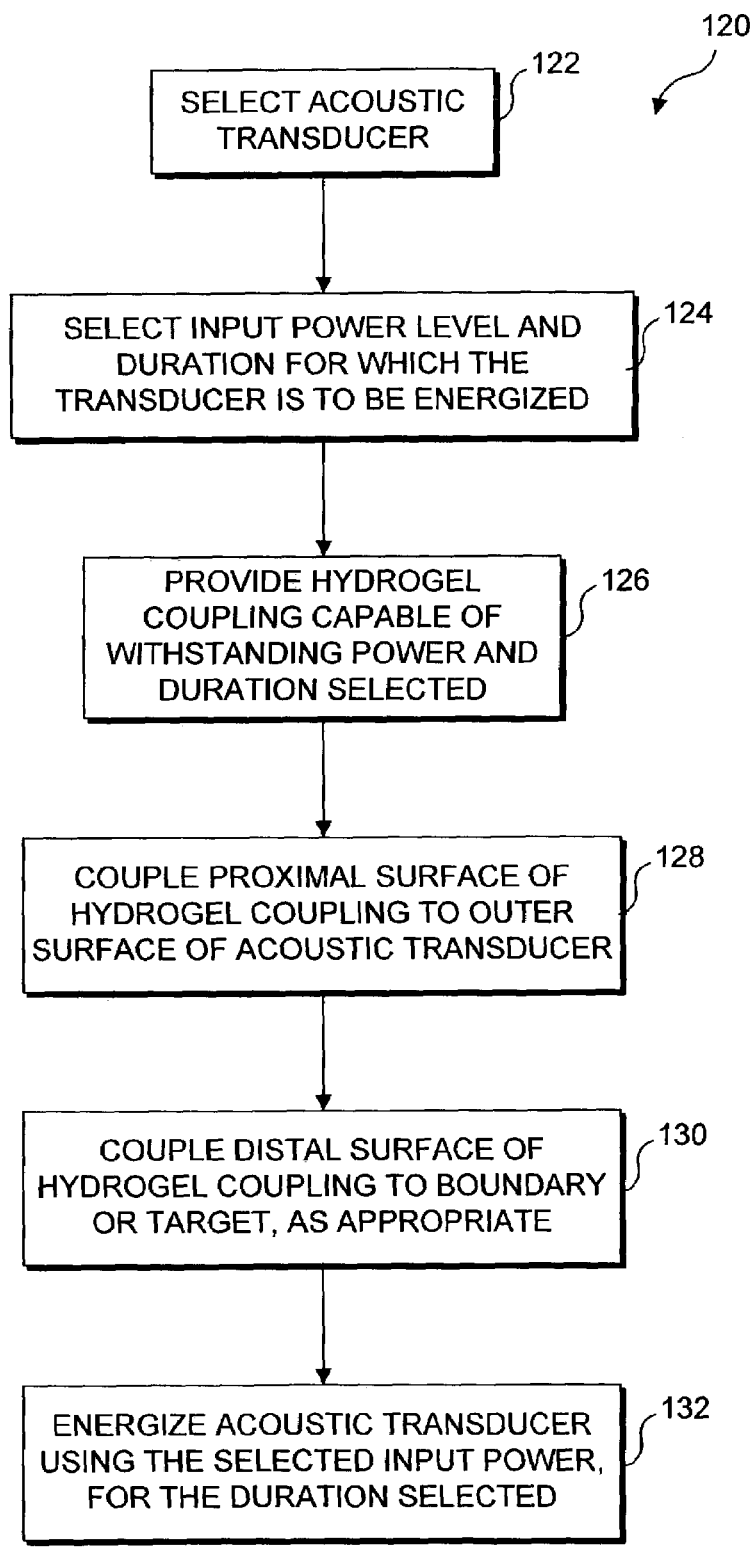
Figure 21:
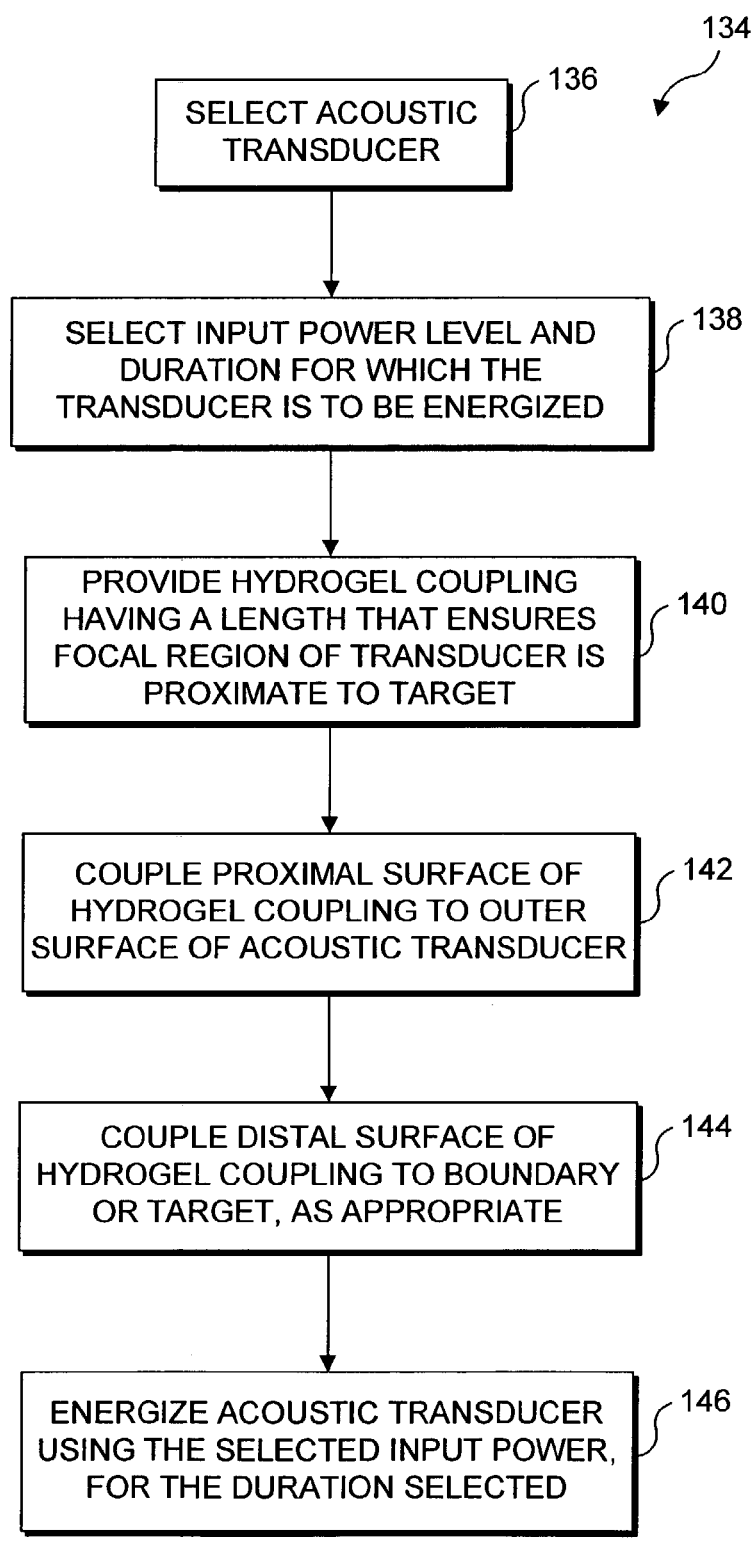
Figure 22:
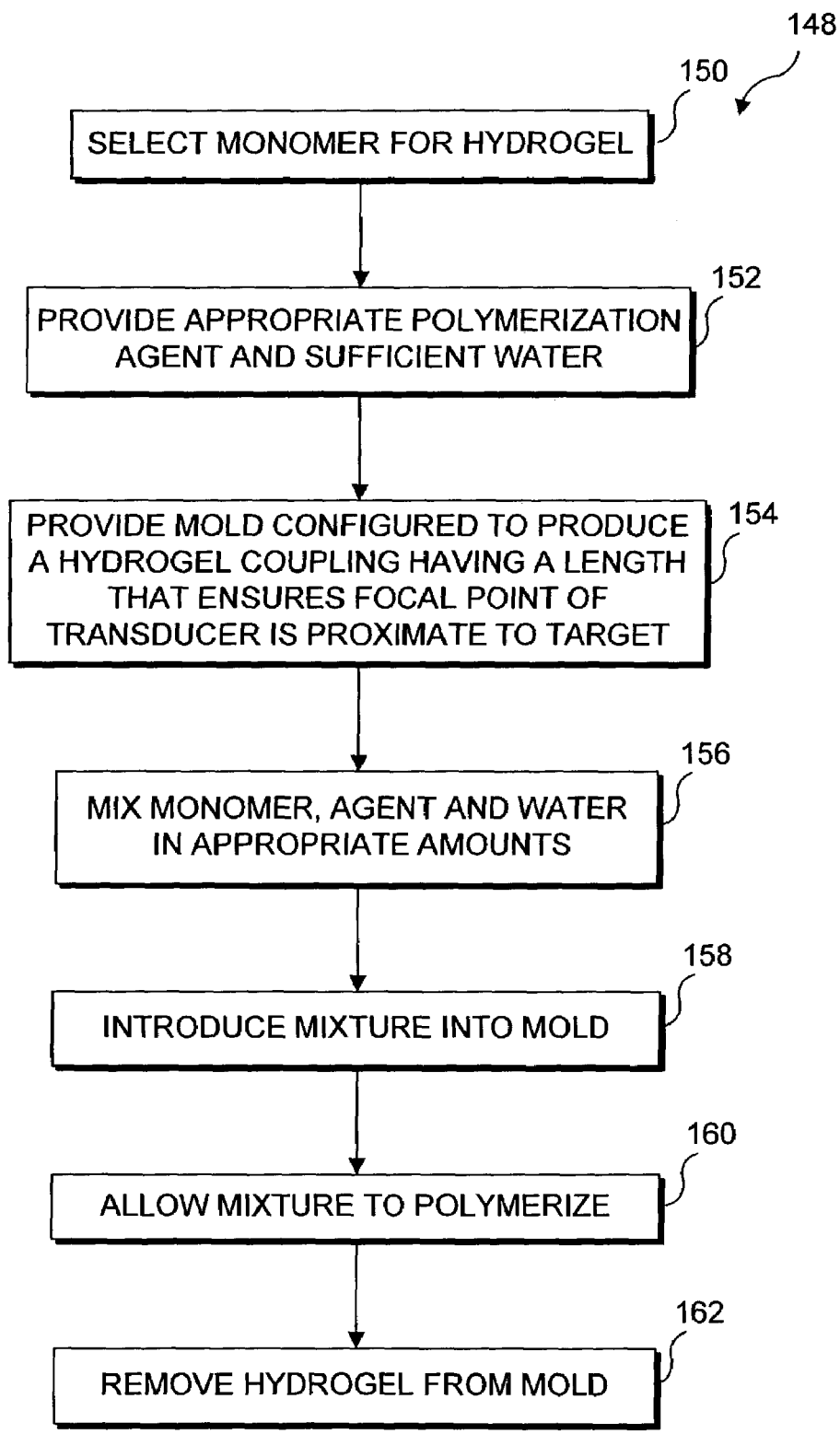
Figure 23:
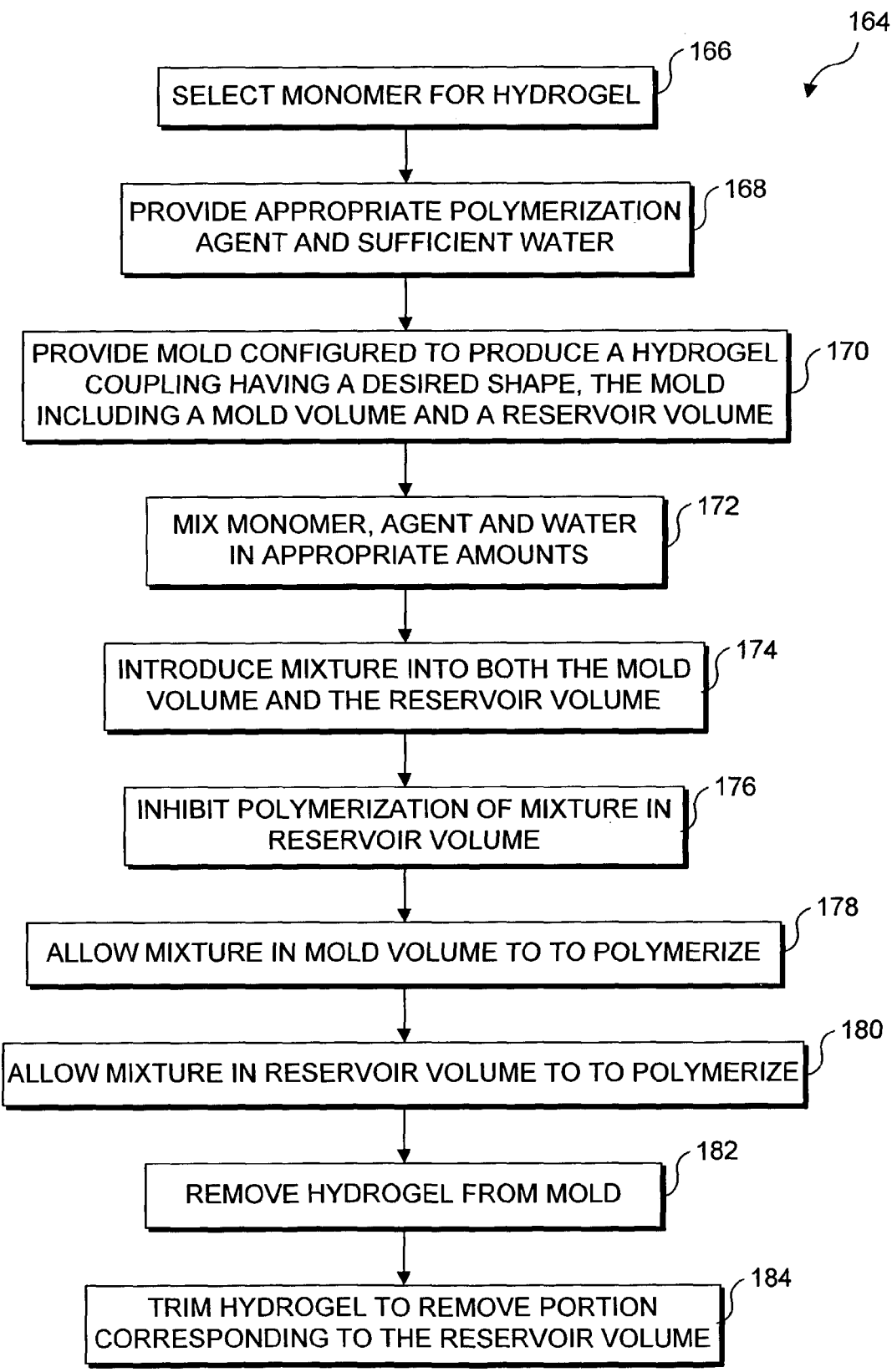

FIG. 7 schematically illustrates each component of a three-part gel mold with the mold in an unassembled state, wherein the mold is configured to produce a substantially cone shaped hydrogel coupling, in accord with the present invention;

FIG. 8 schematically illustrates the three-part gel mold of FIG. 7 in an assembled state;

FIGS. 9A–9C schematically illustrates the three-part gel mold of FIG. 7 being filled with a mixture that polymerizes to form the solid hydrogel coupling;

FIGS. 10A and 10B schematically illustrate the top portion of the three-part gel mold of FIG. 7, to show how the shape of the top portion of the mold determines the shape of the distal surface of the hydrogel coupling produced by the mold;

FIGS. 11A–11D schematically illustrate how changes to the top portion of the three-part gel mold of FIG. 7 affect the shape of the distal surface of the hydrogel coupling produced by the mold;

FIG. 12A schematically illustrates a hydrogel coupling in accord with the present invention, coupled to an acoustic transducer that is mounted on a probe;

FIG. 12B schematically illustrates the hydrogel coupling, acoustic transducer, and probe of FIG. 12A being employed to deliver HIFU to a target location on the dermal layer of a patient;

FIG. 12C schematically illustrates the probe and acoustic transducer of FIGS. 12A and 12B, and a different hydrogel coupling, in accord with the present invention, having a length selected so that a focal region of the acoustic transducer extends to a target underneath the dermal layer of the patient, to deliver HIFU to the sub-dermal target;

FIG. 13A schematically illustrates an exploded view of a probe including an acoustic transducer, a hydrogel coupling, and a restraining housing;

FIG. 13B schematically illustrates the probe of FIG. 13A, with the hydrogel coupling secured to the acoustic transducer by the restraining housing;

FIG. 13C schematically illustrates beam characteristics achieved by the probe of FIG. 13B when the acoustic transducer is energized;

FIG. 14A schematically illustrates an exploded view of the probe of FIG. 13A, a different hydrogel coupling, and a different restraining housing;

FIG. 14B schematically illustrates the probe of FIG. 14A with the different hydrogel coupling secured to the acoustic transducer using the different restraining housing;

FIG. 15A schematically illustrates an acoustic transducer and a hydrogel coupling, in accord with the present invention, the hydrogel coupling having a length that is selected so that a focal region of the acoustic transducer overlaps a desired target, when the outer extent of the distal surface of the hydrogel coupling is brought into contact with a surface overlying the target;

FIGS. 15B–15G each schematically illustrates a hydrogel coupling in accord with the present invention, each different hydrogel having a different length, such that an outer extent of the distal surface of each hydrogel coupling is offset from a focal region of an acoustic transducer by a different amount;

FIG. 16 is a representation of a plurality of Schlieren images of ultrasound field produced by the 3.5 MHz spherically concave transducer of FIG. 1, showing the image when now hydrogel coupling is used in comparison to the images for different length hydrogel couplings;

FIG. 17A schematically illustrates a hydrogel coupling and an external fluid channel, wherein the external fluid channel is employed to hydrate the tip of the hydrogel coupling;

FIG. 17B schematically illustrates a hydrogel coupling, a restraining housing, and an external fluid channel attached to the restraining housing;

FIG. 17C schematically illustrates a hydrogel coupling with an internal fluid channel;

FIG. 18A schematically illustrates a hydrogel coupling with a medicinal agents dispersed within the hydrogel coupling;

FIG. 18B schematically illustrates the hydrogel coupling of FIG. 18A responding to an acoustical beam passing through the hydrogel coupling, showing how the acoustical beam drives the medicinal agent out of the hydrogel coupling;

FIG. 18C schematically illustrates a hydrogel coupling with medicinal agent disposed substantially adjacent to the tip of the hydrogel coupling, and showing an optional fluid channel used to deliver a medicinal agent to the tip;

FIG. 19 schematically illustrates a kit in accord with the present invention, which includes at least a hydrogel coupling, and may optionally include one or more of a restraining housing, instructions, and coupling gel for coupling the hydrogel coupling with an acoustic transducer;

FIG. 20 is a flowchart of the sequence of logical steps employed to utilize a hydrogel coupling in accord with one aspect of the present invention, wherein the hydrogel coupling must be sufficiently robust not to breakdown or melt in HIFU applications;

FIG. 21 is a flowchart of the sequence of logical steps employed to utilize a hydrogel coupling in accord with another aspect of the present invention, wherein the hydrogel coupling has a length that ensures the focal region of the acoustic transducer is proximate the target;

FIG. 22 is a flowchart of the sequence of logical steps employed to produce a hydrogel coupling having a length that ensures the focal region of the acoustic transducer is proximate the target; and FIG. 23 is a flowchart of the sequence of logical steps employed to produce a hydrogel coupling using a mold that has a reservoir and a mold volume, and which accommodates shrinkage of the hydrogel material during polymerization.

DESCRIPTION OF THE PREFERRED EMBODIMENT

The present invention relates to utilizing solid hydrogels as acoustic couplings for clinical applications of ultrasound imaging and therapy, particularly HIFU based therapy. Various aspects of the present invention are disclosed in regard to different embodiments of hydrogel based couplings, methods for using such couplings, and methods for fabricating such couplings.

In the course of developing the present invention, hydrogel couplings in accord with the present invention were evaluated by using such hydrogel couplings to acoustically couple a known acoustic transducer to a variety of targets. As shown in FIG. 1, the specific acoustic transducer employed was a prior art HIFU transducer 10 (SU-102-01) obtained from Sonic Concepts (Woodinville, Wash.). The single element, spherically concave transducer has a center frequency of 3.5 MHz. Its aperture diameter and radius of curvature are 35 mm and 55 mm, respectively, providing an f-number of 1.57. Field mapping of the focal region showed the 6 dB focal width and focal depth to be 1.0 mm and 10.6 mm, respectively. The basic beam characteristics of this acoustic transducer are also shown in FIG. 1.

It should be understood that the present invention is not limited to use with the specific transducer employed in the empirical testing. While other acoustic transducers suitable for HIPU applications may have different specifications (i.e. different aperture diameters, different curvatures, different f-numbers, and different focal regions), many acoustic transducers suitable for HIFU application will exhibit a generally conical shaped beam 12, and a substantially smaller focal region 14.

FIG. 2A shows a hydrogel coupling 16 having a generally conical shape. A lower surface 20 is preferably configured to couple easily in good acoustic contact with an ultrasound transducer. Coupling is most readily achieved if the shape of proximal surface 20 corresponds to the shape of an outer surface of the transducer. However, a mismatch of shapes is not fatal, if sufficient liquid or gel based coupling media is disposed between the outer surface of the transducer and the proximal surface of hydrogel coupling 16. As many HIFU transducers exhibit a generally conical shaped beam, hydrogel couplings having similar shapes are particularly well suited for coupling such transducers to targets. In the empirical studies performed in conjunction with the development of the present invention, the dimensions selected for the cone shaped hydrogel coupling substantially corresponded to the beam dimensions shown in FIG. 1. A hydrogel coupling configured to couple a transducer having different beam dimensions can similarly be produced having dimensions substantially corresponding to the beam dimensions of a specific transducer.

Hydrogel coupling 16 thus substantially corresponds to the beam dimensions of a specific transducer, and a distal surface 18 of hydrogel coupling 16 extends into the focal region of the transducer. While the shape of the hydrogel coupling is not required to substantially match the beam dimensions of a transducer in each aspect of the present invention, in at least some embodiments the dimensions of the hydrogel coupling will substantially match the dimensions of the beam from a selected transducer. As will be described in greater detail below, in some aspects of the present invention, the dimensions of the hydrogel coupling are manipulated specifically to achieve a shape differing from the beam dimensions of a transducer for a specific purpose.

FIG. 2B clearly illustrates that hydrogel coupling 16 substantially corresponds to the focal characteristics of beam 12, which is generated by transducer 10a Transducer 10a differs from transducer 10 in that it is mounted in a base 15, whereas a base is not shown in connection with transducer 10. Those of ordinary skill in the art will recognize that the upper curved surface of a transducer can be accommodated in bases of various sizes and shapes. The base used with transducer 10a facilitates mounting the transducer to a probe, as discussed below.

In FIG. 2B, hydrogel coupling 16 is coupled with transducer 10a. The outer extent of distal surface 18 is disposed proximate focal region 14. It should be understood that hydrogel coupling 16 must be sufficiently robust to endure HIFU applications without melting or damage that would cause distal surface 18 (disposed proximate the focal region) to fail to maintain acoustic coupling with the tissue of a patient. When a hydrogel coupling has dimensions substantially similar to the beam dimensions of a specific transducer, the outer extent or tip of the distal surface of the coupling will be disposed proximate the focal region. That portion of the coupling will be exposed to temperatures significantly greater than those experienced by couplings used to couple imaging transducers to targets. Thus, while a particular coupling material might be acceptable for coupling imaging transducers to targets, the same material will be unable to withstand such use in HIFU applications. Empirical data supports the conclusion that structural failure can occur in couplings made of mediums such as agar. The high temperatures at the tip or outer extent of the distal surface of a coupling adjacent to the focal region of a HIFU transducer can lead to cracking, melting, and loss of structural integrity of the distal surface at that location. Thus, care must be taken when selecting a material to be employed as a coupling for HIFU applications. Many materials suitable for coupling an imaging transducer to a target will be unable to withstand the temperatures encountered in coupling HIFU transducers to a target.

One aspect of the present invention is directed to a hydrogel coupling wherein the specific hydrogel is selected to ensure that the hydrogel coupling is sufficiently robust for use in HIFU applications. The material selected must have sufficient transmissivity to avoid overheating as a result of absorbing ultrasound energy. In other words, it is important that the coupling material deliver as much as possible of the HIFU energy to the focal region and not absorb the energy.

The energy deposited in a coupling medium disposed proximate the focal region of a transducer can be calculated as follows:

$$T = \frac{2\alpha It}{\rho c_m} + T_0 \quad (1)$$

where T is the temperature after a time t, $T_0$ is the temperature at the start of HIFU application (t=0), I is the temporal average intensity, t is time, $\alpha$ is the absorbance coefficient in Nepers/cm, $\rho$ is the density of the medium, and $c_m$ is the specific heat per unit mass. The majority of attenuation (more than 95%) can be attributed to absorbance, and as a result, the absorbance is assumed to be approximately equal to the attenuation.

The above equation is useful in the investigation of different coupling agents for HIFU devices that require the position of the HIFU focus to be close to the tip of the coupling agent. Typical values that could be used in the above equations are as follows:

HIFU intensity, I, on the order of 1000 W/cm$^2$

HIFU application time, t, on the order of 100 seconds

Density, $\rho$, on the order of 1 g/ml

Specific heat per unit mass, $c_m$, is on the order of 6.5 J/g for PA

Attenuation coefficient, $\alpha$, on the order of 0.035 Np/cm, at 3 MHz for PA

Therefore, the temperature rise determined from the above equation is:

$$T-T_0 \approx 1000° C.$$

This relatively great temperature increase does not occur in clinical settings. The counteracting parameters are thermal convection dissipating energy out of the HIFU focus, and cooling due to blood flow. However, the equation does demonstrate that a large temperature increase in the coupling medium can be expected at or near the focus. A robust coupling medium must be able to handle large temperature increases by having a high melting point, as well as having a low attenuation that reduces the temperature increase.

According to a first aspect of the present invention, hydrogels used to produce hydrogel couplings are selected to ensure that when the hydrogel coupling is used in conjunction with an acoustic transducer in accord with certain parameters, and with a portion of the hydrogel coupling disposed proximate the focal region of the transducer, the dimensionally stable hydrogel mass forming the coupling has a melting point that is sufficiently high, and an acoustical absorbance that is sufficiently low to enable the dimensionally stable hydrogel mass to maintain its structural integrity. The parameters are: (a) the transducer is energized for a period ranging from about 1 second to about 100 seconds; and, (b) the intensity of the acoustical beam generated by the transducer ranges from about 100 W/cm$^2$ to about 10,000 W/cm$^2$.

Empirical testing has determined that acrylamide monomers can be employed to produce PA hydrogels that fall within the ranges noted above. The structure and properties of PA have been extensively researched for the past 30 years. Currently, its most common biomedical application is for gel electrophoresis, for the separation of charged macromolecules. While there are many different hydrogels available, PA hydrogels exhibit other desirable properties, in addition to having characteristic within the ranges noted above. PA hydrogels can have very high WC, ranging from 70% to more than 90% water by weight and can be prepared relatively easily and quickly at room temperature. The mechanical properties of PA hydrogels, and therefore their acoustic properties, can be varied in a straightforward manner simply by changing the overall concentration of acrylamide monomer in the material. In addition, PA has been used for a variety of biomedical applications and has been shown in many studies to have very good biocompatibility.

An important consideration for any blood-contacting device is its resistance to causing thrombosis on its surface. Experiments have shown PA to exhibit no platelet adhesion. A recent clinical study that investigated the use of a PA-based blood filtration technique showed the material to have good blood-compatibility, with no signs of hemolysis or blood clotting. Moderate material costs and straightforward manufacturing methods enable inexpensive, custom-designed, disposable HIFU coupling devices to be made from PA gels.

FIGS. 3A–3C schematically represent three PA gel test plugs fabricated in order to gain empirical data about hydrogel couplings suitable for HIFU applications. Each sample has a diameter of 2.5 cm and a height of approximately 3 cm. Stiffness and transparency increase with acrylamide concentration. Note that plug 22a was formed using acrylamide monomer at a concentration of 10%, and is slightly opaque as indicated by the shading in this plug. Plug 22b was formed using acrylamide monomer at a concentration of 15%, and is more transparent, as indicated by the diminished shading in plug 22b. Plug 22c was formed using acrylamide monomer at a concentration of 20%, and is substantially transparent, as indicated by the lack of shading. The procedure for producing the gel plugs is explained in detail below. This procedure was also employed for producing generally cone-shaped PA hydrogel couplings, as well as PA hydrogel couplings having other shapes. Substantially transparent couplings have the advantage of enabling a clinician to see through the coupling, to better view the target area.

A summary of the process for making the PA gels employed in the present invention is set forth below. Those of ordinary skill in the art will recognize that modifications to the process described below can readily be made.

To form a rigid, 3-D hydrogel, a cross-linking agent is used to hold the long polymer chains together in a matrix. Bisacrylamide, also known as N,N'-methylenebis(acrylamide), is the cross-linker preferably used in the formation of PA. The bisacrylamide molecule consists of two acrylamide residues joined at their amide groups by a methyl group. The two acrylamide residues participate in the polymerization reaction as though they were two independent monomers.

For PA gels used for electrophoresis, this buffering agent is used to adjust the pH of the gel to pH 8. In PA gel electrophoresis, the pH of the medium is important in determining the charges on the biological molecules used. The pH of the solution may affect the protonation state of the —$NH_2$ groups of the acrylamide monomers. With respect to the present invention, the influence of pH was not investigated, but was simply kept constant for each gel. Because the production of PA electrophoresis gels is well known, the same pH level was employed in making PA for use in the present invention. The buffer solution employed was Trizma base, also called Tris(hydroxymethyl)aminomethane, and Trizma hydrochloride, also called Tris(hydroxymethyl)aminomethane hydrochloride.

Ammonium persulfate (APS) was employed as an initiator for polymerization, since it is a source of free radicals. In solution, APS forms the persulfate ion, $S_2O_8^{2-}$. This common, water-soluble initiator is one of the strongest chemical oxidizing agents known.

TEMED, also known as N,N,N',N'-Tetramethylethylenediamine catalyzes the radical formation process. APS and TEMED form a redox system, where APS is the oxidizing agent and TEMED is the reducing agent. Although the redox initiation mechanism of the persulfate-TEMED system is not well understood, it is likely that TEMED forms a free radical in addition to the persulfate free radical, and that both radicals are involved in the initiation process.

The APS-TEMED redox system is a type of thermal initiator. For a 15%-weight in volume PA gel, the maximum temperature during polymerization was about 61° C. The proportion of APS-TEMED initiator to total solution determines the rate at which polymerization occurs. Polymerization rate increases with an increasing proportion of the initiator. In addition, reaction rate and temperature increase with the concentration of acrylamide in solution. Thus, higher-concentration gels tend to polymerize at a faster rate and reach higher temperatures during polymerization than lower-concentration gels.

The physical properties of PA vary according to the concentration of acrylamide monomer in the gel. Acrylamide concentrations used in gathering empirical data relating to the present invention ranged from 10% to 20% weight in volume (w/v). The percent concentration was determined by the ratio of the mass of total acrylamide to the volume of pre-polymerized solution. An aqueous solution of 40% w/v acrylamide with a 19:1 monomer to cross-linker ratio (LIQUI-GEL; ICN Biomedicals, Aurora, Ohio) was used to prepare the gels. The hydrogels were formed in solution by the free radical, chain-reaction polymerization process noted above. The initiated solution was transferred to either a cylindrical mold (see FIGS. 3A–3C), or to a substantially cone-shaped mold (see FIGS. 7 and 8) which are described below. The cylindrical mold was primarily employed to produce plugs for material testing and characterization, while the cone shaped mold was employed to produce hydrogel couplings that were tested with the acoustic transducer described in connection with FIG. 1. With respect to the cylindrical mold, the mold was kept upright, so that the gel's top face formed parallel to the bottom face. Each gel plug was allowed to polymerize for about 25 to 30 minutes. The resulting cylindrical gel plugs were 2.5 cm in diameter and approximately 3 cm in height (FIGS. 3A–3C). A difficulty associated with using hydrogels is that they dehydrate when left exposed to ambient air, and swell when placed in water due to increased absorption of the water. Therefore, the gels were either tested within one hour after polymerization, or stored in vacuum-sealed, plastic bags for later use.

Bulk Properties

Water content (WC) and density were measured for gels with varying acrylamide concentrations. WC was determined for acrylamide concentrations of 10%, 15%, and 20% w/v. Six gel samples were tested for each concentration. Density was measured for concentrations of 10%, 12.5%, 15%, 17.5%, and 20% w/v. Seven gel samples were tested for each concentration.

The WC was determined by comparing the mass of the hydrated gel immediately after polymerization, $m_h$, to the mass of the dehydrated gel, $m_d$. Water content was calculated using the following formula:

$$WC = \frac{m_h - m_d}{m_h} \times 100 \qquad (2)$$

The measured values of the bulk and acoustic properties of PA gel at various concentrations are listed in Table 1.

TABLE 1

| Acryl. Conc. | WC(%) N = 6 | ρ(g/cm³) N = 7 | c(m/s) N = 7 | Z(Mrayl) N = 7 | α(dB/cm) N = 7 | | | | |
|---|---|---|---|---|---|---|---|---|---|
| | | | | | 1 MHz | 2 MHz | 3 MHz | 4 MHz | 5 MHz |
| 10% | 87.0 +/− 0.8 | 1.024 +/− 0.006 | 546 +/− 2 | 1.583 +/− 0.008 | 0.077 +/− 0.039 | 0.115 +/− 0.033 | 0.206 +/− 0.031 | 0.300 +/− 0.037 | 0.437 +/− 0.058 |
| 12.5% | — | 1.031 +/− 0.005 | 558 +/− 2 | 1.607 +/− 0.008 | 0.099 +/− 0.027 | 0.179 +/− 0.043 | 0.259 +/− 0.043 | 0.386 +/− 0.037 | 0.523 +/− 0.051 |

TABLE 1-continued

| Acryl. Conc. | WC(%) N = 6 | ρ(g/cm³) N = 7 | c(m/s) N = 7 | Z(Mrayl) N = 7 | α(dB/cm) N = 7 | | | | |
|---|---|---|---|---|---|---|---|---|---|
| | | | | | 1 MHz | 2 MHz | 3 MHz | 4 MHz | 5 MHz |
| 15% | 81.6 +/− 1.0 | 1.038 +/− 0.004 | 568 +/− 2 | 1.628 +/− 0.005 | 0.121 +/− 0.027 | 0.185 +/− 0.042 | 0.331 +/− 0.037 | 0.495 +/− 0.042 | 0.698 +/− 0.112 |
| 17.5% | — | 1.043 +/− 0.005 | 582 +/− 2 | 1.649 +/− 0.009 | 0.119 +/− 0.051 | 0.249 +/− 0.036 | 0.376 +/− 0.033 | 0.540 +/− 0.036 | 0.760 +/− 0.029 |
| 20% | 76.0 +/− 1.1 | 1.052 +/− 0.003 | 595 +/− 2 | 1.679 +/− 0.004 | 0.142 +/− 0.020 | 0.236 +/− 0.047 | 0.413 +/− 0.046 | 0.647 +/− 0.066 | 0.873 +/− 0.041 |

The density, ρ of the gel immediately after polymerization was calculated by dividing the mass of the gel by its volume. Mass was measured with an electronic scale, and volume was measured using a water displacement technique.

The WC of PA decreased from 87% to 76% as a linear function of increasing acrylamide concentration. The density of the gel was found to be slightly greater than the density of water, increasing from 1.02 to 1.05 g/ml as a linear function of increasing acrylamide concentration.

Acoustic Properties of PA Hydrogels

Sound speed, c(m/s), acoustic impedance, Z(Mrayl), and attenuation, α (dB/cm), were measured for gels of five different acrylamide concentrations: 10%, 12.5%, 15%, 17.5%, and 20% w/v. For each concentration, seven gel samples were tested at 25° C. In addition, acoustic properties were measured for one 15% w/v acrylamide gel sample at different temperatures, ranging from 23° C. to 45° C.

A pulse transmission technique was used to measure the attenuation coefficient and speed of sound in the PA samples. Calculations were based on the well known substitution method, where two acoustic paths are compared. The sample path contained the gel sample with approximately two centimeters of water on either side, and the reference path contained only water. The attenuation coefficient was measured at frequencies of 1 MHz to 5 MHz.

Figure 4B:
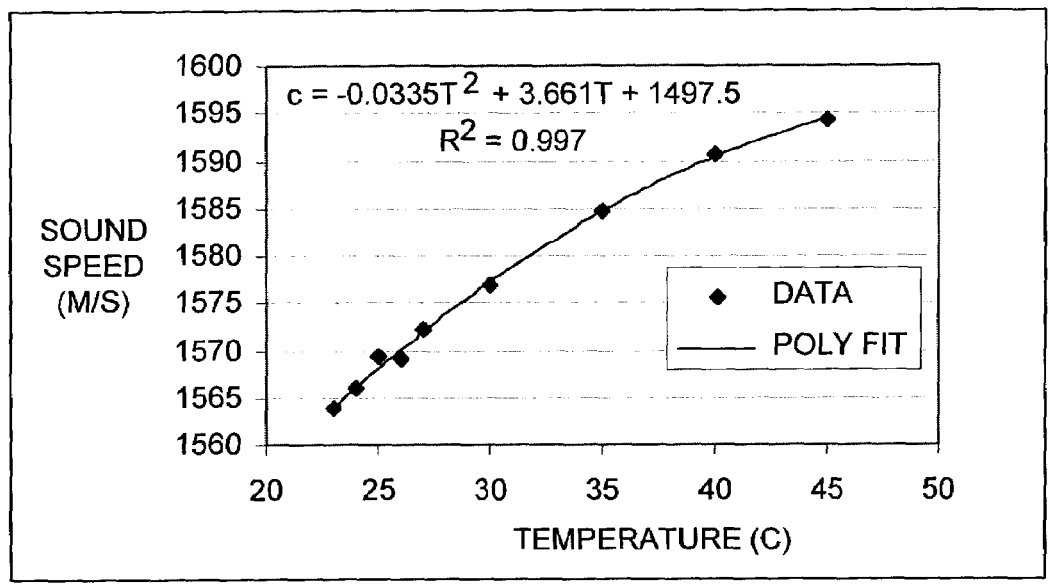
FIG. 4B is a graphical representation of sound speed in PA hydrogel couplings versus acrylamide concentration, showing a polynomial data fit.
Figure 5A:
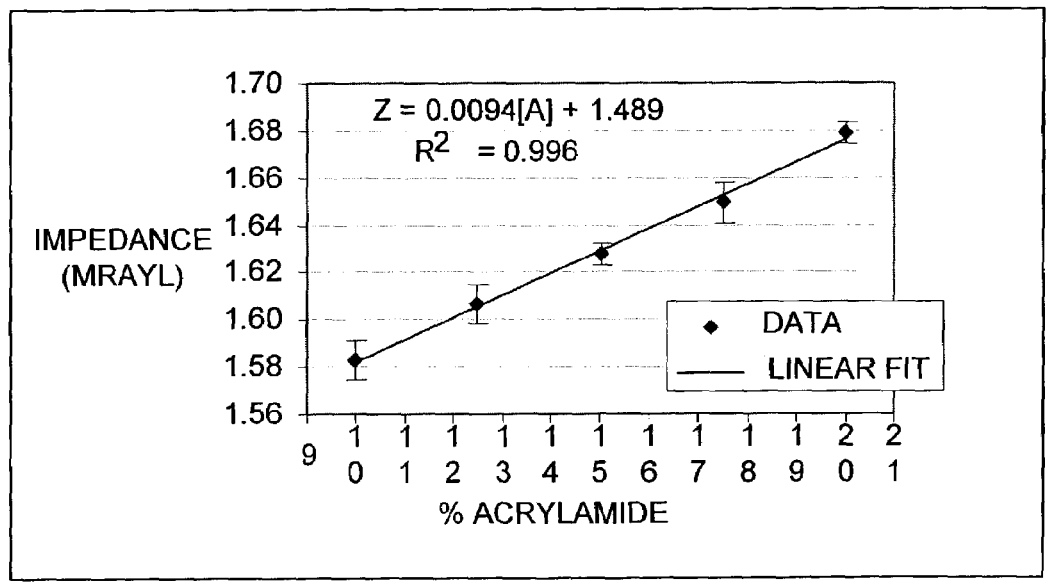
FIG. 5A is a graphical representation of the acoustic impedance of PA hydrogel couplings versus acrylamide concentration, showing a linear data fit.
Figure 5B:
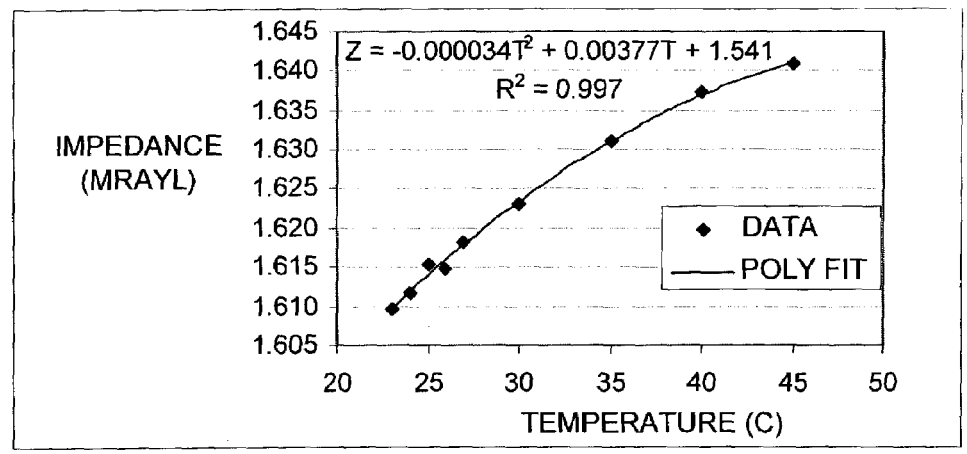
FIG. 5B is a graphical representation of the acoustic impedance of PA hydrogel couplings versus acrylamide concentration, showing a polynomial data fit.
Figure 6A:
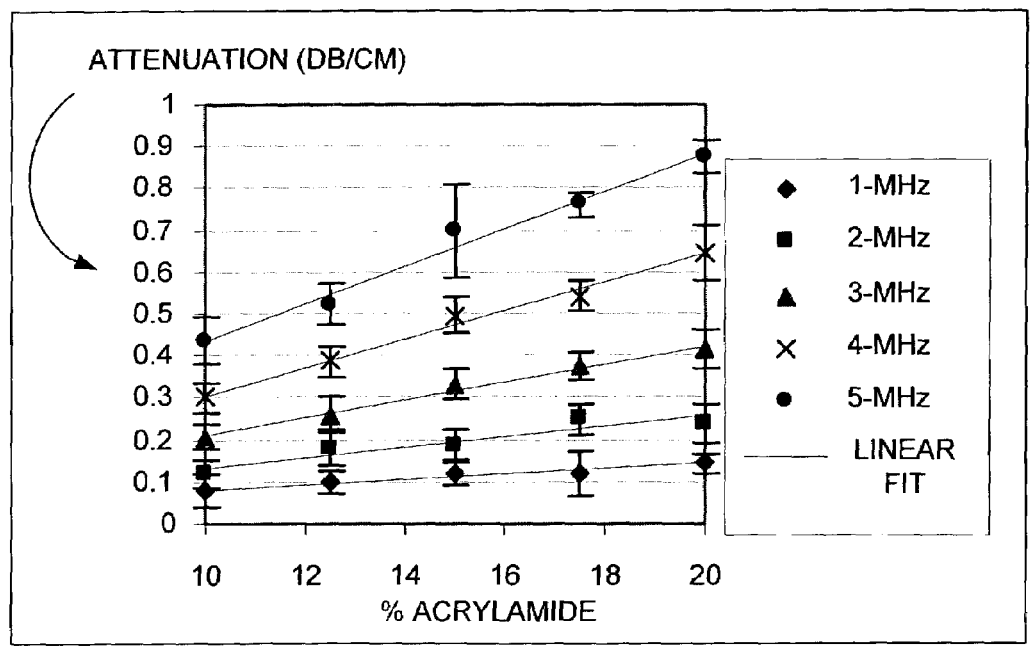
FIG. 6A is a graphical representation of the attenuation coefficient of PA hydrogel couplings versus acrylamide concentration, showing a linear data fit.
Figure 6B:
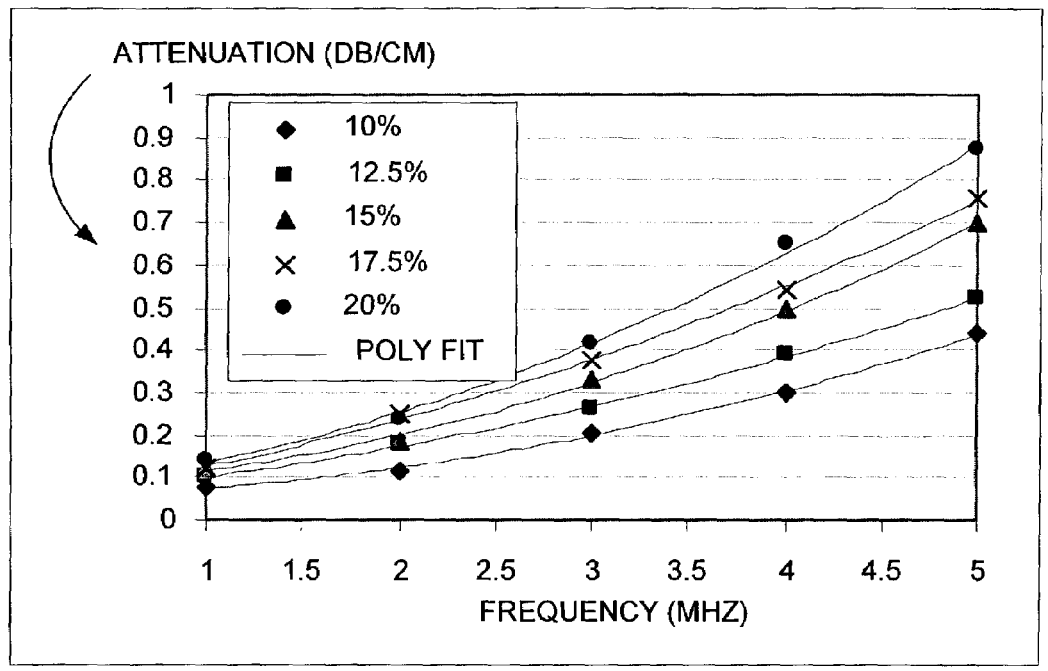
FIG. 6B is a graphical representation of the attenuation coefficient of PA hydrogel couplings versus frequency for different acrylamide concentrations, showing a polynomial data fit.
Figure 6C:
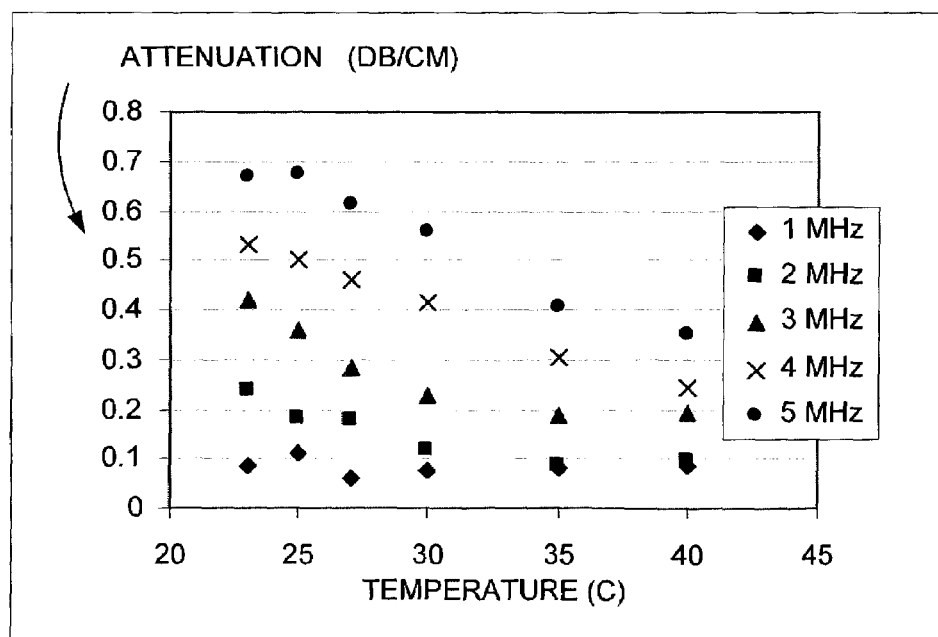
FIG. 6C is a graphical representation of the attenuation coefficient of a 15% PA hydrogel coupling versus gel temperature.

For the concentration range tested, the acoustic properties of PA increased as linear functions of increasing acrylamide concentration. Sound speed ranged from 1546 to 1595 m/s for 10% and 20% w/v gels, respectively (FIG. 4A). Acoustic impedance ranged from 1.58 to 1.68 Mrayl (FIG. 5A). Attenuation ranged from 0.08 to 0.14 dB/cm at 1 MHz (FIG. 6A). Linear regression showed that the rate of increase in attenuation coefficient with concentration was larger at higher frequencies. A plot of attenuation coefficient versus frequency showed that attenuation was not a linear function of frequency (FIG. 6B). While a second order polynomial fit the data well, the data did not show a strictly frequency-squared dependence, as is the case for water. Sound speed and impedance were shown to increase with temperature, while attenuation was shown to decrease with temperature (FIGS. 4B, 5B, and 6C).

Thermal Properties of PA Hydrogels

The thermal conductivity, k(W/m/° C.), and specific heat capacity, $C_p$(J/kg/° C.), of PA were measured by monitoring the thermal dissipation of a heat impulse. A nickel-chromium heating wire was pulled taut through the center of a custom-made measurement cell. The initiated PA solution was poured into the measurement cell (approximately a cube with 5 cm edges) and allowed to polymerize into the hydrogel. Four needle T-type thermocouples (Omega Engineering Inc., Stamford, Conn.) were inserted into the gel parallel to the heating wire. The thermocouples were placed at different radial distances from the wire, ranging from 4 mm to 11 mm. The exact distances from their junctions to the heating wire were measured using an ultrasound imaging system (a model HDI 1000™ from ATL Corp., Bothell, Wash.). A LabVIEW™ (National Instruments, Austin, Tex.) program controlled the length of the current pulse delivered to the heating wire, and recorded the four thermocouple temperatures over time.

The following equation, which is based on Fourier's law of heat conduction in cylindrical coordinates, was used to determine the radial temperature distribution at some time after heating:

$$\ln(Tt) = -\frac{r^2}{4\chi t} + \ln\left(\frac{Q}{4\pi L \rho C_p \chi}\right) \qquad (3)$$

$$\chi = \frac{k}{\rho C_p}$$

where T(° C.) was the temperature elevation from ambient at some radial distance, r(m), from the wire; t(s) was the time after heating at which the measurement was made; Q(J) was the total deposited heat (J); L(m) was wire length; ρ (kg/m³) was the density of the gel; and χ (m²/s) was the thermal diffusivity of the gel. This equation assumes that the time until measurement was significantly larger than the heating time, and that the diameter of the wire is negligible.

Thermal properties were measured for three different acrylamide concentrations: 10%, 15%, and 20% w/v. Heat was applied for 5s, which resulted in a temperature rise of about 1° C. at 4 mm from the wire. Ln(Tt) versus r²/t was graphed for each of the four thermocouple positions. By fitting a line to the data, the slope and intercept were used to calculate $C_p$ and k. Two independent experiments were performed for each acrylamide concentration.

The thermal conductivity and specific heat capacity did not vary measurably with acrylamide concentration over the range tested. The overall average thermal conductivity and specific heat capacity of PA, 0.84 W/m/° C. and 6470 J/kg/° C. respectively, were found to be slightly higher than the corresponding values for water, 0.61 W/m/° C. and 4178 J/kg/° C.

Power Efficiency

Power efficiency was measured to determine the effectiveness of the PA coupler in delivering focused ultrasound into water. Overall power efficiency, $E_{Overall}$, of the transducer-coupler device was defined as the ratio of output acoustic power delivered to a water bath, to input electrical power supplied to the transducer. $E_{Overall}$ was defined as:

$$E_{Overall} = E_{Transducer} \times E_{Coupler} \qquad (4)$$

where $E_{Transducer}$ was the transducer efficiency, and $E_{Coupler}$ was the coupler efficiency. $E_{Transducer}$ was determined by measuring output acoustic power for the transducer without any coupler attached. The efficiency of the coupler could then be calculated from Equation 3. A test was performed to determine how acrylamide concentration affected the power efficiency of the device. For comparison, a water-filled coupling cone, with the same dimensions as the full-length gel couplers, was also tested. The couplers were attached to the 3.5 MHz HIFU transducer. A reflecting radiation force balance (a model UPM-DT-IOE™ from Ohmic Instruments Co., Easton, Md.) was used to measure the output acoustic power for five input electrical power levels, ranging from 2 W to 90 W. Output power was plotted versus input power, and overall efficiency was calculated as the slope of the best-fit line to the data. Efficiency was measured for full-length, convex-tip, gel couplers with 10%, 15%, and 20% acrylamide concentrations. These data were compared to theoretical efficiencies based on the attenuation in the gel. The theoretical efficiency of the gel, $E_{Coupler\ Theory}$, was calculated using the following equation:

$$E_{Coupler.\ Theory} = \exp(-2\alpha d) \quad (5)$$

where $\alpha$ (nepers/cm) was the measured attenuation coefficient of the gel at 3.5 MHz, and d(5.2 cm) was the length of the gel. For this calculation, it was assumed that loss of acoustic power was due only to attenuation in the gel coupler. Attenuation due to water was assumed to be negligible.

Table 2 lists the measured and theoretical power efficiency for the different couplers. The transducer efficiency was measured at 55.8%. Attaching the 5.2 cm gel cone to the transducer dropped the overall efficiency to between 22.4% and 28.6%, for 20% and 10% acrylamide concentrations, respectively. Normalizing the overall efficiency to the transducer efficiency showed the gel cones to have coupler efficiencies from 40.1% to 51.3%. For comparison, the coupler efficiency of the water-filled cone was measured to be 65.3%. The measured coupler efficiency of the gel cone was 14% to 23% less than its calculated theoretical efficiency. The attenuation coefficient used for PA at 3.5 MHz was calculated from polynomials fit to the measured attenuation data, and was found to be 0.029, 0.046, and 0.059-nepers/cm, for 10%, 15%, and 20% acrylamide, respectively.

TABLE 2

| Coupler Type | Measured Overall Efficiency (%) | Measured Coupler Efficiency (%) | Theoretical Coupler Efficiency (%) |
|---|---|---|---|
| No Coupler | 55.8 | 100 | 100 |
| Water-Filled Cone | 36.4 | 65.3 | 100 |
| 10% Acryl. 5.2 cm | 28.6 | 51.3 | 74.2 |
| 15% Acryl. 5.2 cm | 26.3 | 47.3 | 61.7 |
| 20% Acryl. 5.2 cm | 22.4 | 40.1 | 53.8 |

Beneficial Properties of PA Hydrogel Couplings

The favorable acoustic properties of PA make the material a good coupling medium for applications of both therapeutic and diagnostic ultrasound. The gel is a homogeneous material that consists mostly of water. It has low attenuation, with sound speed and acoustic impedance similar to that of tissue. Due to the gel's ideal impedance, minimal reflections will occur at the gel-tissue interface. An advantage of the PA coupling is that its acoustic properties vary linearly with acrylamide concentration. Acoustic characterization of the material is, therefore, a straightforward process, if gel concentration is known, making it relatively easy to match the impedance of specific tissue in a patient's body.

A PA coupler has several properties that make it desirable for HIFU applications. The acoustic properties vary linearly with acrylamide concentration, which allows for straightforward modification of the gel's acoustic and impedance characteristics. The PA coupler's acoustic impedance can be matched to a particular tissue simply by varying the acrylamide concentration. In transcutaneous HIFU applications, reducing impedance mismatch at the gel-tissue interface can diminish the occurrence of skin burns caused by reflections and standing waves. Matching sound speed of a PA coupling to a specific tissue type can reduce adverse effects caused by refraction of the ultrasound beam at the gel-tissue interface. In some HIFU applications, this issue may be of substantial importance, since a shift in the position of the focus can result in undesirable damage to surrounding normal tissue.

Due to its low attenuation, PA couplings have acceptable power transfer efficiency. Since efficiency decreases with increasing coupler length, it might be advantageous to use transducers with short focal distances for superficial HIFU treatments.

Beneficial Properties of Hydrogel Couplings

Hydrogels in general have the advantages associated with being a solid coupling material. Unlike water-filled couplers, there are no problems with containment and leakage of the hydrogel coupling medium. Using an appropriate mold, couplings can be formed to fit to a specific HIFU transducer. Their shape and size can also be modified for a particular application. For transcutaneous applications, the depth of the focus below the tissue interface can be adjusted by using couplings with different lengths, as described in detail below. For intraoperative hemostasis applications, the shape and height of the cone tip can be varied to achieve more effective treatments. Modifying the tip shape is done by selecting an appropriate mold, as described below.

The coupling need not be permanently attached to a HIFU transducer. Unlike prior art aluminum couplers, which were held to the PZT element by epoxy, the coupling can be temporarily attached with a thin layer of water or sonography gel and readily replaced with a different coupling. The disposable nature of the coupling is ideal for HIFU applications in which the focus is near the distal tip of the coupling. While a gel may ultimately sustain some HIFU or mechanically related damage to its tip, this damage does not permanently impair the transducer for farther use, since a new coupling can readily replace the current one.

While PA hydrogels have been empirically tested and proven capable of being used for HIFU applications, it is expected that other hydrogel materials, and or mixtures of different hydrogels will be identified as being sufficiently robust to be employed as a coupler for HIFU applications. For example, poly(2-hydroxyethyl methacrylate), or pHEMA, is likely to be a useful hydrogel for HIFU applications.

The functional tests noted above were performed on conical PA couplings designed to fit to the transducer described in connection with FIG. 1 (a 3.5 MHz, spherically concave, single element, HIFU transducer with a 5.5 cm focal length and a 3.5 cm aperture diameter). Such conically shaped couplings were produced using a custom-built three part mold 30, which is shown in FIGS. 7 and 8. The gel cones had spherically convex bases that matched the curvature of the transducer. Full-length or truncated conical plastic housings held the gel couplers to the transducer. Full-length, flat-tip cones were 4.9 cm long, which placed the center of the HIFU focus 0.6 cm from the tip. The tip shape and height can be varied to place the focus at different distances from the tip. For the majority of the tests, convex tips 0.3 cm in height were used, which placed the center of the HIFU focus about 0.3 cm from the tip.

Referring once again to FIGS. 7 and 8, the three part mold includes a base portion 32, a middle portion 34, and a top portion 36. Base portion 32 is configured to match the concave outer surface of the transducer, and thus includes a concave surface 40. Base portion 32 can be modified to achieve a mold configured to produce a hydrogel coupling for a different transducer having a distal surface with a different shape or dimension. Preferably, the proximal surface of the hydrogel coupling produced by mold 30 corresponds to the shape of the outer surface of the transducer with which the hydrogel mass is to be used. FIG. 7 shows a hydrogel coupling 38 seated in base portion 32.

Middle portion 34 is substantially cone shaped, to match the focal characteristics of the exemplary transducer, as shown in FIGS. 1 and 2B, discussed above. Of course, other shapes can be employed, as desired. Top portion 36 includes a tip molding portion 42, which as described in detail below can be modified to achieve a desired shape for the outer extent or tip of the distal surface of a hydrogel coupling produced using mold 30. Top portion 36 also includes a drip channel 44 coupling a reservoir 46 in fluid communication with a mold volume 48. Mold volume 48 is defined by base portion 32, middle portion 34 and top portion 36.

The function of reservoir 46 is illustrated in FIGS. 9A–9C. In FIG. 9A, a liquid mixture (such as the acrylamide monomer based mixture disclosed above) is introduced into reservoir 46 of mold 30. In FIG. 9B, the mixture within the mold volume is allowed to polymerize, while polymerization of the mixture in the reservoir is inhibited. An exemplary technique to prevent polymerization is agitating or stirring the mixture in the reservoir. Those of ordinary skill in the polymer arts will appreciate that other techniques for inhibiting the mixture in reservoir may be appropriate. For example, some polymer reactions are initiated by illuminating with light of an appropriate wavelength (dental polymers used to replace mercury amalgams are an example). Thus, inhibiting polymerization might involve preventing light of that wavelength from reaching the mixture in the reservoir, while light is applied to the mixture in the mold volume. It should be noted that while the PA hydrogel described in detail above represents an exemplary hydrogel, mold 30, and variants of mold 30, can be used to form other hydrogel materials into acoustic couplings, and thus the technique for inhibiting the polymerization in the reservoir will be dictated by the initiator used to induce polymerization in the specific reaction and material employed.

As hydrogels polymerize, they shrink. The solid portion shown in FIG. 9B represents the original mixture introduced into the mold volume. If no additional mixture was introduced into the mold volume, the shape of the finished hydrogel would not be as desired (i.e., an upper tip 50 would be missing). However, as the mixture originally introduced into the mold volume polymerizes and shrinks, additional liquid mixture from reservoir flows into the mold volume and polymerizes.

Once the mold volume is filled with polymerized mixture (i.e., a hydrogel) the mixture in the reservoir is allowed to polymerize. The mold is taken apart, and the portion of the hydrogel within the reservoir (and within the drip channel coupling the reservoir to the mold volume) can be trimmed away.

It should be noted that while mold 30 performed admirably for laboratory purposes, mass production of hydrogel couplings will likely be achieved using molds specifically adapted for high speed production. Clearly, the present invention is not limited to manufacture specifically using mold 30, or even to three part molds.

FIGS. 10A–11D provide details on how modifying top portion 36 can enable hydrogel couplings having distal surfaces of different configurations to be achieved. To achieve good coupling with a target or a boundary disposed between the target and the transducer, the distal surface of the hydrogel coupling should closely conform to the surface of the target or boundary, respectively. While coupling gels can be used to fill any gaps, closely matched surfaces enhance coupling and ease of use.

In FIGS. 10A and 10B, top portion 36 comprises an outer ring 36a and an inner portion 36b. Inner portion 36b includes the reservoir and the drip channel described above (reference numbers omitted to simplify the Figure, see FIG. 8). A surface 54a determines the shape of the tip of the distal surface of the hydrogel coupling produced.

While not specifically shown, ring 36a and middle portion 34 can rotatably couple together using threads in an area 62. The dimensions of ring 36a and middle portion 34 can be configured at area 62 such that ring 36a is press fit onto middle portion 34 securely enough so that the mold does not come apart while molding the PA material, but loosely enough so that the ring can be removed after the mold is used, to disassemble the mold. Also, note that ring 36a and inner portion 36b are notched at area 64, to enable inner portion 36b to be held securely in position, as shown in FIG. 10B.

Figure 11A:
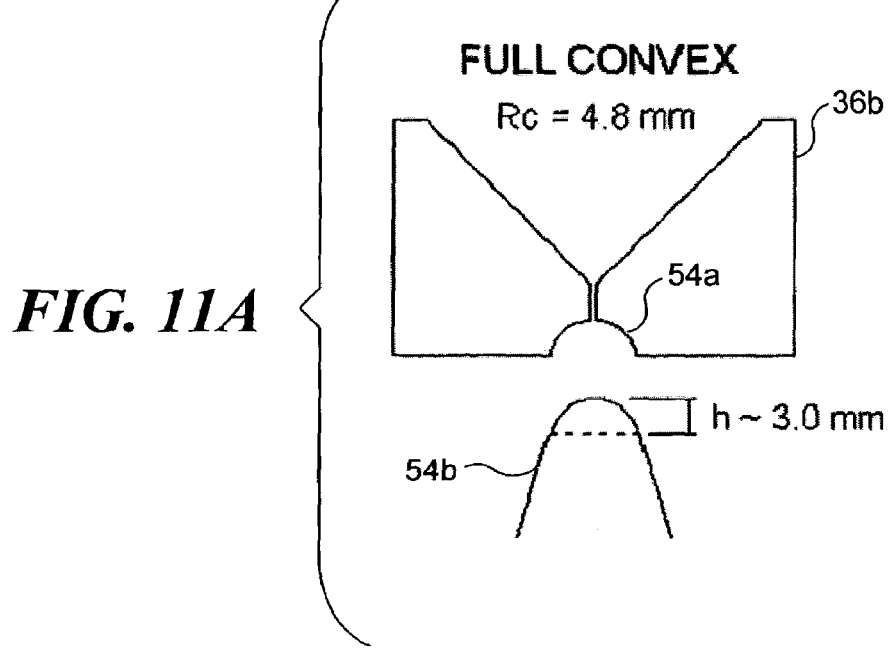

FIGS. 11A–11D illustrate inner portions of different shapes, and the tip of the distal surface of a hydrogel coupling that is achieved using that inner portion. In FIG. 11A, inner portion 36b can be employed to produce a hydrogel coupling having a tip on distal surface 54b that is a full convex, corresponding to a full concave surface 54a on the bottom of inner portion 36b. A useful radius of curvature for surface 54a is about 4.8 mm.

In FIG. 11B, inner portion 36c can be employed to produce a hydrogel coupling having a tip on distal surface 56b that is a short convex, conforming to a short concave surface 56a on the bottom of inner portion 36c. A useful radius of curvature for concave surface 56a is 7.3 mm.

In FIG. 11C, inner portion 36d can be employed to produce a hydrogel coupling having a tip on distal surface 58b that is flat, conforming to a flat 58a, while in FIG. 11D, inner portion 36e can be employed to produce a hydrogel coupling having a tip on distal surface 60b that is concave, conforming to a convex surface 60a. A useful radius of curvature for convex surface 60a is 7.3 mm.

It should be understood that the dimensions of the curvatures suggested above are intended to be exemplary, and not limiting on the present invention. Of course, other shapes can be employed in a mold to achieve any desired hydrogel coupling shape.

FIG. 12A illustrates an exemplary use of hydrogel couplings in accord with the present invention. In a probe 65, a conical hydrogel coupling 66 is attached to an acoustic transducer 68, mounted to a handle 70. A lead 72 couples the transducer to a power supply 74. In FIG. 12B, probe 65 is being used to apply HIFU to a target proximate a dermal layer 76 of a patient (not otherwise shown). Focal region 14 is proximate to (within) the dermal layer. In such a configuration, the distal surface of coupling 66 is disposed proximate to the focal region of the transducer. Thus, it is important for the hydrogel to be sufficiently robust to maintain its structural integrity during application of HIFU therapy. It should be understood that probe 65 could be used inside a patient's body, inserted via a body cavity or incision, and is not limited to external use. The significance of probe 65 is that the focal region of the transducer is disposed proximate to the distal surface of the hydrogel coupling so that the tip of the hydrogel coupling is immediately adjacent to the treatment site. Thus, the HIFU can be easily aimed by observing the tip of the distal surface of the hydrogel coupling.

A probe 65a shown in FIG. 12C is different, in that the distal surface of a hydrogel coupling 66a is not disposed immediately adjacent to or proximate to the focal region of the transducer. Hydrogel coupling 66a is significantly shorter, such that when the tip of the hydrogel coupling lies against the dermal layer of the patient, the focal region of the transducer is within a subcutaneous target 78. Selecting an even shorter hydrogel coupling would enable the focal region to penetrate further below the dermal layer and deeper into the subcutaneous target, while selecting a longer hydrogel coupling will bring the focal region closer to the dermal layer. Thus if the location of the target is known, a hydrogel coupling of an appropriate length can be selected, so as to ensure that the focal region of the transducer is disposed proximate to the desired target. When shorter hydrogel couplings are used, less robust hydrogels can be employed, because the distal surface is no longer proximate to the focal region, where the highest temperatures are likely to be encountered.

FIGS. 13A–13C illustrate how a restraining housing 80a can be used to removably secure hydrogel coupling 66 to transducer 68. FIG. 13A is an exploded view illustrating how restraining housing 80a fits over hydrogel coupling 66. In FIG. 13B, the restraining housing has been secured to transducer 68 (or handle 70), thereby mounting hydrogel coupling 66 in place. Restraining housing 80a is open at its conical end, so that a tip of distal surface 82 of the hydrogel coupling is exposed and extends beyond the restraining housing. FIG. 13C shows transducer 68 being energized, resulting in acoustical waves 84. Note that the focal region of the transducer is proximate to the upper extent of distal surface 82 of the hydrogel coupling.

FIGS. 14A and 14B show a shorter restraining housing 80b being used to couple a shorter hydrogel coupling 86 to the same transducer. FIG. 14A is an exploded view illustrating how restraining housing 80b fits over hydrogel coupling 86, while FIG. 14B is an assembled view. FIG. 14B also includes beam dimension 12 and focal region 14, illustrating that a distal surface 88 of hydrogel coupling 86 is not disposed proximate to the focal region.

FIGS. 15A–15G further illustrate how the length of a hydrogel coupling can be selected to enable the focal region to be disposed adjacent to a target. In FIG. 15A, a hydrogel coupling 90 is shown positioned over transducer 68. Coupling 90 has a length 92. By providing a plurality of couplers 94a–94f, each having a different length, the position of the focal region relative to a distal surface of the hydrogel coupling can be varied. Longer hydrogel couplings (e.g., hydrogel coupling 94e) will result in distal surfaces of the couplings being disposed closer to the focal region. Shorter couplings (e.g., coupling 94a) will result in distal surfaces of the hydrogel couplings being disposed farther away from the focal region. As shown in FIG. 12C, the shorter the coupling, the farther away the focal region will be from the distal surface of the coupling, which will be brought into contact with the surface of intervening tissue.

FIG. 16 illustrates Schlieren images obtained using hydrogel couplings of varying lengths. Schlieren imaging was used to visualize the ultrasound field emitted from the HIFU transducer with the hydrogel coupler attached, and to determine if the gel coupler was in any way distorting the HIFU field. Four 15% gel cones of different shapes were tested: a 2 cm truncated cone; a 3 cm truncated cone; a full-length cone with flat tip; and a full-length gel cone with convex rounded tip. A collimated beam of light passed through an optically transparent tank containing degassed water. The HIFU beam was directed into the water tank, perpendicular to the light beam axis. The light leaving the tank was focused and filtered, and the image was displayed on a screen.

The images obtained showed that the HIFU field was essentially unchanged by the presence of the various gel couplers. For the full-length, flat and round tip couplers, the image of the ultrasound field seemed to bleed down into the shadow of the coupler tip. This effect was probably caused by diffraction of the light beam.

As noted above, when the distal surface of a hydrogel coupling is disposed proximate the focal region, particularly in HIFU applications, intense temperatures and pressures can damage the distal surface of the hydrogel coupling. As hydrogel couplings include a large amount by weight of water, such temperatures and pressures have been empirically shown to dry out the distal surfaces, leading to damage to the surfaces. Thus, an aspect of the present invention is the incorporation of means to hydrate (or maintain the hydration of) the distal surfaces of the hydrogel couplings. FIGS. 17A–17C illustrate several structures that can be used to achieve such hydration. In FIG. 17A, a fluid channel 98 is coupled with a water supply (not shown), and the other end of the fluid channel is disposed adjacent to a tip 95 of the distal surface of hydrogel 96. In FIG. 17B, a fluid channel 98a is attached to a restraining housing 100 and is coupled with a water supply (not shown); the other end of the fluid channel is disposed adjacent to tip 95 of the distal surface of hydrogel 96. In the embodiment illustrated in FIG. 17C, a fluid channel 102 is disposed within hydrogel coupling 96a. Fluid channel 102 is coupled with a water supply (not shown), and the other end of the fluid channel is disposed adjacent to a tip 95a of the distal surface of hydrogel 96a, to enable the surface to be hydrated.

A unique advantage of using a hydrogel is the possibility of introducing medication, such as antibiotics, into the hydrogel coupling, and to administer such medications where the hydrogel coupling contacts the tissue of a patient. During surgery, the hydrogel coupler can be used to transfer antibiotics, in addition to ultrasound, into the treatment site. FIGS. 18A–18C illustrate several structures that can be used to achieve such medication. In FIG. 18A, a hydrogel coupling 96b has a medicinal agent 104 distributed throughout the hydrogel. The agent can be added after the hydrogel is produced. Hydrogels include many channels within the hydrogel where such medicinal agents can be absorbed and stored. It is expected that if the polymerization is not detrimental to the medicinal agent, the medicine can be added before the hydrogel is produced. In FIG. 18B, energizing a transducer coupled to the hydrogel causes some of the medicinal agent to be "pushed out" of tip 95b of the distal surface of the hydrogel coupling. The effect of the therapeutic agent could be either synergistic with, or independent of HIFU. Thus, the therapeutic outcome can either be enhanced exponentially, or arithmetically, depending on the choice of the therapeutic agent and the HIFU dose.

In FIG. 18C, medicinal agent 104 has been distributed proximate to a tip 95c of the distal surface, rather than throughout hydrogel coupling 96c. A fluid channel 98a is shown as an optional element and can be used to hydrate tip 95c of the distal surface of hydrogel coupling 96c, or even to deliver additional medicinal agents. If desired, fluid channel 98a could be used as the sole method of delivering a medicinal agent.

As shown in FIG. 19, yet another aspect of the present invention is a kit 110 containing components to be used for acoustically coupling an ultrasound transducer with a target. Kit 110 includes at least a hydrogel coupling 112, having a proximal surface configured to be disposed adjacent to an ultrasound transducer, and a distal surface configured to acoustically couple with at least one of a target and a boundary associated with the target. The kit also includes at least a sealed package 122 configured to maintain the hydrogel coupling in a hydrated condition until removed from the sealed package in preparation for use. The sealed package can be hermetically sealed and/or vacuum-sealed to maintain the contents of the package in a sterile state and avoid loss of hydration of the hydrogel coupler.

Optionally, kit 110 includes instructions 118 for using the hydrogel coupling to couple an ultrasound transducer with a target, to facilitate an application of HIFU therapy. The instructions may also inform users how to maintain the distal surface of the dimensionally stable hydrogel coupling in a hydrated condition.

Another optional elements is coupling gel 116, which is a semisolid or fluidic coupling medium used to enhance an acoustic coupling of the proximal surface of the hydrogel coupling to an outer surface of an ultrasound transducer that is used to administer the HIFU therapy. Yet another optional element of such a kit is a retaining housing 114, configured to removably couple the hydrogel coupling with an ultrasound transducer.

Ideally, couplers with different cone heights and impedance would be available to the physician. Accordingly, kits containing different length hydrogel couplers (see FIGS. 15B–15G) will preferably be available.

FIGS. 20–23 are flow charts illustrating sequences of logical steps employed in carrying out the present invention. FIG. 20 illustrates the steps for using a hydrogel coupling sufficiently robust to withstand the ultrasound intensities to be employed; FIG. 21 illustrates the steps for ensuring that a focal region of a transducer is proximate a target; FIG. 22 illustrates the steps for making a hydrogel coupling configured to ensure that a focal region of a transducer is proximate a target; and FIG. 23 illustrates the steps for producing a hydrogel that accommodates for shrinkage during polymerization.

Referring to FIG. 20, a flow chart 120 begins in a block 122, in which a specific acoustic transducer is selected. In a block 124, an input power level and a duration for energizing the ultrasound transducer are selected. A block 126 refers to providing a hydrogel coupling that is capable of maintaining its structural integrity when used to couple the ultrasound transducer with at least one of the target and a physical boundary associated with the target under the input power level and duration selected. In at least one embodiment, the hydrogel coupling provided has a length that will ensure that a focal region of the ultrasound transducer is disposed proximate the target.

In a block 128, the proximal surface of the hydrogel coupling is coupled with an outer surface of the ultrasound transducer, and in a block 130, the distal surface of the hydrogel coupling is coupled with at least one of the target and a physical boundary separating the target from the distal surface of the hydrogel coupling. A restraining housing can be used to secure the hydrogel coupling. Finally, in a block 132, the ultrasound transducer is energized at the selected input power level and duration. Additional steps can include hydrating the distal surface of the dimensionally stable hydrogel mass, to prevent damage to the tip of the distal surface of the dimensionally stable hydrogel mass by the HIFU, and/or delivering a medicinal agent to at least one of the target and the physical boundary, after coupling the distal surface of the dimensionally stable hydrogel mass to at least one of the target and the physical boundary. Referring now to FIG. 21, a flow chart 134 begins in a block 136, where a specific ultrasound transducer to be employed is selected. In a block 138, an input power level and a duration are selected to energize the ultrasound transducer. A block 140 indicates that a hydrogel coupling is provided having a length that will ensure that a focal region of the ultrasound transducer is disposed proximate to the target.

In a block 142, the proximal surface of the hydrogel coupling is coupled with an outer surface of the ultrasound transducer, and in a block 144, the distal surface of the hydrogel coupling is coupled with at least one of the target and a physical boundary separating the target from the distal surface of the hydrogel coupling. As noted above, a restraining housing can be used to secure the hydrogel coupling. Finally, in a block 146, the ultrasound transducer is energized at the selected input power level and duration.

Flow chart 148 of FIG. 22 illustrates the steps involved in producing a hydrogel coupling having a length that will ensure a focal region of a specific ultrasound transducer is disposed proximate to the target. In a block 150 the monomer, or mixture of monomers are selected from which the hydrogel will be produced. As discussed above, acrylamide monomers can be beneficially employed. However, the invention is not so limited, and other monomer(s) can alternatively be employed. In a block 152, an agent is provided for inducing polymerization of the at least one monomer, providing a quantity of water sufficient to hydrate the quantity of the selected monomer(s).

In a block 154, a mold configured to form a hydrogel coupling having the desired size and shape is provided. The mold is configured to produce a hydrogel coupling having a length that ensures a focal region of a specific ultrasound transducer is disposed proximate to the target, generally as described above. In a block 156, the monomer, agent, and water are mixed together in the appropriate amounts. Those of ordinary skill in the art will recognize that many different components for producing hydrogels are known. In a block 158, the mixture is introduced into the mold. In a block 160, the mixture is allowed to polymerize, and in a block 162, the hydrogel coupling is removed from the mold.

Referring now to FIG. 23, a flow chart 164 illustrates the logical steps for producing a hydrogel coupling using a mold with a reservoir to accommodate shrinkage. In a block 166, the monomer is selected, and in a block 168, an agent for inducing polymerization of the monomer, and water, are provided. In a block 170, a mold configured to form a hydrogel coupling having the desired size and shape is provided. The mold includes both a mold volume corresponding to the size and shape of the desired hydrogel coupling, and a reservoir in fluid communication with the mold volume.

In a block 172, the monomer, the agent, and water are mixed together in appropriate amounts. In a block 174, the mixture is introduced into the mold. In a block 176, the mixture in the reservoir is inhibited from polymerization, while in a block 178 the mixture in the mold volume is allowed to polymerize.

After the mixture in the mold volume polymerizes, the mixture in the reservoir is allowed to polymerize, as indicated in block 180. In a block 182, the hydrogel coupling is removed from the mold, and the hydrogel coupling is trimmed in a block 184, to remove the portion corresponding to the reservoir portion and interconnection to the mold.

One beneficial property of hydrogels is that they are dimensionally stable, solid appearing materials, in sharp contrast to the semi-solid, paste-like coupling gels frequently used to couple imaging transducers to tissue. In the claims that follow, the term "dimensionally stable hydrogel mass" has been employed to emphasize this property.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A hydrogel coupling adapted to be disposed between an ultrasound transducer and a target, wherein the ultrasound transducer exhibits a characteristic focal length that separates a focal region where ultrasound waves emitted from the ultrasound transducer are focused, from the ultrasound transducer, the hydrogel coupling being configured to acoustically couple an ultrasound transducer with a physical boundary associated with a target, wherein the physical boundary is disposed between the ultrasound transducer and the target, said hydrogel coupling comprising:
   (a) a rigid dimensionally stable hydrogel mass having a proximal surface configured to be disposed adjacent to an ultrasound transducer; and
   (b) a distal surface configured to acoustically couple with a physical boundary associated with a target, such that a distance between said proximal surface and an outer extent of said distal surface is selected to ensure that a focal region of an ultrasound transducer to which the hydrogel mass is coupled, is disposed proximate to a desired target.

2. The hydrogel coupling of claim 1, wherein said proximal surface is further configured to conform to an outer surface of an ultrasound transducer.

3. The hydrogel coupling of claim 2, wherein said proximal surface is convex in shape.

4. The hydrogel coupling of claim 1, wherein said distal surface is convex in shape.

5. The hydrogel coupling of claim 1, wherein said distal surface is concave in shape.

6. The hydrogel coupling of claim 1, wherein said dimensionally stable hydrogel mass is generally cone shaped.

7. The hydrogel coupling of claim 1, wherein said dimensionally stable hydrogel mass is shaped generally as a truncated cone.

8. The hydrogel coupling of claim 1, further comprising a retaining housing configured to removably couple said dimensionally stable hydrogel mass to an ultrasound transducer by engaging an outer surface of said dimensionally stable hydrogel mass, so as to cause said proximal surface to engage the ultrasound transducer.

9. The hydrogel coupling of claim 8, wherein said retaining housing substantially conforms to the outer surface of said dimensionally stable hydrogel mass.

10. The hydrogel coupling of claim 8, wherein said retaining housing substantially encloses said dimensionally stable hydrogel mass, except for the outer extent of said distal surface and said proximal surface.

11. The hydrogel coupling of claim 8, wherein said retaining housing comprises a polymer.

12. The hydrogel coupling of claim 1, wherein said dimensionally stable hydrogel mass comprises poly(2-hydroxyethyl methacrylate).

13. The hydrogel coupling of claim 1, wherein said dimensionally stable hydrogel mass comprises polyacrylamide.

14. The hydrogel coupling of claim 13, wherein an amount of acrylamide monomer employed to produce said dimensionally stable hydrogel mass is selected so that an acoustical impedance of said dimensionally stable hydrogel mass substantially matches an acoustical impedance of at least one of a target and a physical boundary associated with a target with which said dimensionally stable hydrogel mass is to acoustically couple.

15. The hydrogel coupling of claim 1, wherein said dimensionally stable hydrogel mass has a melting point that is sufficiently high, and an acoustical absorbance that is sufficiently low to enable the dimensionally stable hydrogel mass to maintain its structural integrity when coupled with an ultrasound transducer, where:
   (a) said distal surface of said dimensionally stable hydrogel mass is disposed proximate to a focal region of the ultrasound transducer;
   (b) the ultrasound transducer is energized for a period ranging from about 1 second to about 100 seconds; and
   (c) an intensity of an acoustical beam generated by the ultrasound transducer ranges from about 100 W/cm$^2$ to about 10,000 W/cm$^2$.

16. The hydrogel coupling of claim 1, further comprising means to hydrate said distal surface of said dimensionally stable hydrogel mass.

17. The hydrogel coupling of claim 16, wherein said means comprises a fluid channel having a proximal end configured to be coupled to a water supply, and having a distal end disposed adjacent to said distal surface.

18. The hydrogel coupling of claim 1, further comprising a fluid channel having a proximal end configured to be coupled to a fluid supply, and having a distal end disposed adjacent to said distal surface.

19. The hydrogel coupling of claim 18, wherein at least a portion of said fluid channel is disposed within said dimensionally stable hydrogel mass.

20. The hydrogel coupling of claim 18, further comprising a retaining housing configured to removably couple said dimensionally stable hydrogel mass with an ultrasound transducer, and wherein at least a portion of said fluid channel is supported by said retaining housing.

21. The hydrogel coupling of claim 20, wherein at least a portion of said fluid channel is integral to said retaining housing.

22. The hydrogel coupling of claim 1, further comprising means to deliver a medicinal agent proximate to said distal surface of said dimensionally stable hydrogel mass.

23. The hydrogel coupling of claim 22, wherein said means comprises a fluid channel having a proximal end configured to be coupled to a fluid supply including a medicinal agent, said fluid channel having a distal end disposed adjacent to said distal surface.

24. The hydrogel coupling of claim 22, wherein said means comprises a quantity of medicinal agent disposed within said dimensionally stable hydrogel mass, such that said medicinal agent is distributed proximate to the outer extent of said distal surface of the dimensionally stable hydrogel mass.

25. The hydrogel coupling of claim 1, wherein a shape of said dimensionally stable hydrogel mass substantially corresponds to an ultrasound beam shape of an ultrasound transducer with which said dimensionally stable hydrogel mass is intended to be used.

26. The hydrogel coupling of claim 1, wherein the dimensionally stable hydrogel mass is configured to removably couple with an ultrasound transducer, such that after use, the dimensionally stable hydrogel mass can readily be removed and replaced with a different dimensionally stable hydrogel mass.

27. The hydrogel coupling of claim 1, further comprising means for removably coupling one of a plurality of different size dimensionally stable hydrogel masses to an ultrasound transducer, for providing different distances between the proximal surface and the outer extent of the distal surface of each different size of the different size dimensionally stable hydrogel masses.

28. A hydrogel coupling adapted to be disposed between an ultrasound transducer and at least one of a target and a physical boundary associated with a target, to acoustically couple the ultrasound transducer with at least one of a target and a physical boundary associated with a target, said hydrogel coupling comprising:
(a) dimensionally stable hydrogel mass having:
(i) a proximal surface configured to be disposed adjacent to an ultrasound transducer; and
(ii) a distal surface configured to acoustically couple with at least one of a target and a physical boundary associated with a target; and
(b) a fluid channel having a proximal end configured to be coupled to a fluid supply, and having a distal end disposed adjacent to said distal surface.

29. The hydrogel coupling of claim 28, wherein a length between said proximal surface and an outer extent of said distal surface is selected to ensure that a focal region of the ultrasound transducer is disposed proximate to a target.

30. The hydrogel coupling of claim 28, wherein the proximal surface is further configured to conform to an outer surface of the ultrasound transducer.

31. The hydrogel coupling of claim 28, wherein said distal surface is one of convex in shape, concave in shape, and flat in shape.

32. The hydrogel coupling of claim 28, wherein the dimensionally stable hydrogel mass is substantially transparent, such that the dimensionally stable hydrogel mass does not block a view of the target when in use.

33. The hydrogel coupling of claim 28, further comprising a retaining housing configured to removably couple said dimensionally stable hydrogel mass to an ultrasound transducer by engaging an outer surface of said dimensionally stable hydrogel mass, so as to cause said proximal surface to engage the ultrasound transducer.

34. The hydrogel coupling of claim 28, wherein a shape of said dimensionally stable hydrogel mass substantially corresponds to a shape of an ultrasound beam produced by the ultrasound transducer with which said dimensionally stable hydrogel mass is intended to be used.

35. The hydrogel coupling of claim 28, further comprising means to deliver a medicinal fluid proximate to said distal surface of said dimensionally stable hydrogel mass.

36. The hydrogel coupling of claim 35, wherein said means to deliver a medicinal fluid comprises the fluid channel, where the proximal end of the fluid channel is configured to be coupled to a medicinal fluid supply.

37. The hydrogel coupling of claim 35, wherein said means to deliver a medicinal fluid comprises a quantity of a medicinal fluid that has been absorbed into said dimensionally stable hydrogel mass.

38. The hydrogel coupling of claim 28, wherein the fluid channel is formed in the dimensionally stable hydrogel mass.

39. The hydrogel coupling of claim 33, wherein the retaining housing comprises the fluid channel.

40. The hydrogel coupling of claim 28, further comprising means for removably coupling one of a plurality of different size dimensionally stable hydrogel masses to an ultrasound transducer, for providing different distances between the proximal surface and the outer extent of the distal surface of each different size of the different size dimensionally stable hydrogel masses.

41. The hydrogel coupling of claim 28, wherein the dimensionally stable hydrogel mass is configured to removably couple with an ultrasound transducer, such that the dimensionally stable hydrogel mass is removed and discarded after each use.

42. A hydrogel coupling adapted to be disposed between an ultrasound transducer and a target, to acoustically couple an ultrasound transducer with at least one of a target and a physical boundary associated with a target, wherein the physical boundary is disposed between the ultrasound transducer and the target, said hydrogel coupling comprising a dimensionally stable hydrogel mass, the dimensionally stable hydrogel mass being characterized by:
(a) having a proximal surface configured to be disposed adjacent to an ultrasound transducer;
(b) having a distal surface configured to acoustically couple with at least one of a desired target and a physical boundary associated with a desired target, wherein a distance between said proximal surface and an outer extent of said distal surface is selected to ensure that a focal region of an ultrasound transducer to which the hydrogel mass is coupled, is disposed proximate to a desired target; and
(c) being configured to removably couple with an ultrasound transducer, such that if the distance between the proximal surface and the outer extent of the distal surface of the dimensionally stable hydrogel mass does not ensure a focal region of an ultrasound transducer coupled with the dimensionally stable hydrogel mass is disposed proximate to a desired target, then the dimensionally stable hydrogel mass is readily removed and replaced with a different dimensionally stable hydrogel mass having a different distance between its proximal surface and its outer extent of the distal surface, to ensure that a focal region of an ultrasound transducer coupled with the different dimensionally stable hydrogel mass is disposed proximate to a desired target.

43. A hydrogel coupling adapted to be disposed between an ultrasound transducer and at least one of a target and a physical boundary associated with a target, to acoustically couple the ultrasound transducer with at least one of a target and a physical boundary associated with a target, said hydrogel coupling comprising:
(a) a dimensionally stable hydrogel mass having:
(i) a proximal surface configured to be disposed adjacent to an ultrasound transducer; and (ii) a distal surface configured to acoustically couple with at least one of a target and a physical boundary associated with a target, wherein the dimensionally stable hydrogel mass has a melting point that is sufficiently high, and an acoustical absorbance that is sufficiently low to enable the dimensionally stable hydrogel mass to maintain its structural integrity when coupled with the ultrasound transducer, when:
 (1) said distal surface of said dimensionally stable hydrogel mass is disposed proximate to a focal region of the ultrasound transducer;
 (2) the ultrasound transducer is energized for a period ranging from about 1 second to about 100 seconds; and
 (3) an intensity of an acoustical beam generated by the ultrasound transducer ranges from about 100 W/cm$^2$ to about 10,000 W/cm$^2$;

(b) such that if the distance between the proximal surface and the outer extent of the distal surface of the dimensionally stable hydrogel mass does not ensure a focal region of an ultrasound transducer coupled with the dimensionally stable hydrogel mass is disposed proximate to a desired target, then the dimensionally stable hydrogel mass can readily be removed and replaced with a different dimensionally stable hydrogel mass having a different distance between its proximal surface and its outer extent of the distal surface to ensure that a focal region of an ultrasound transducer coupled with the different dimensionally stable hydrogel mass is disposed proximate to a desired target.

44. A hydrogel coupling adapted to be disposed between an ultrasound transducer and a target, to acoustically couple an ultrasound transducer with at least one of a target and a physical boundary associated with a target, wherein the physical boundary is disposed between the ultrasound transducer and the target, said hydrogel coupling comprising a dimensionally stable hydrogel mass, the dimensionally stable hydrogel mass being characterized by:
 (a) having a proximal surface configured to be disposed adjacent to an ultrasound transducer;
 (b) having a distal surface configured to acoustically couple with at least one of a target and a physical boundary associated with a target, such that a distance between said proximal surface and an outer extent of said distal surface is selected to ensure that a focal region of an ultrasound transducer to which the hydrogel mass is coupled, is disposed proximate to a desired target; and
 (c) having a shape that substantially corresponds to an ultrasound beam shape of an ultrasound transducer with which said dimensionally stable hydrogel mass is intended to be used, at least over a portion of the ultrasound beam shape over which the dimensionally stable hydrogel mass is intended to be coincident.

45. A hydrogel coupling adapted to be disposed between an ultrasound transducer and a target, to acoustically couple an ultrasound transducer with a physical boundary associated with a target, wherein the physical boundary is disposed between the ultrasound transducer and the target, said hydrogel coupling comprising a dimensionally stable hydrogel mass, the dimensionally stable hydrogel mass being characterized by having a shape that substantially corresponds to a shape of a portion of an ultrasound beam generated by an ultrasound transducer with which said dimensionally stable hydrogel mass is intended to be used, where a proximal extent of the portion is defined by the ultrasound transducer, and a distal extent of the portion is defined by the physical boundary.

\* \* \* \* \*

UNITED STATES PATENT AND TRADEMARK OFFICE
CERTIFICATE OF CORRECTION

PATENT NO. : 7,070,565 B2  Page 1 of 1
APPLICATION NO. : 10/449819
DATED : July 4, 2006
INVENTOR(S) : Vaezy et al.

It is certified that error appears in the above-identified patent and that said Letters Patent is hereby corrected as shown below:

Col. 1 the paragraph under "Government Rights" beginning at line 8 should be replaced in its entirety with the following:

--This invention was made with government support under grant N00014-96-1-0630 awarded by the Department of the Navy, and grant 5 R01 EB000292-04 awarded by the National Institutes of Health. The government has certain rights in the invention.--

Signed and Sealed this

Sixteenth Day of September, 2008

JON W. DUDAS
*Director of the United States Patent and Trademark Office*